(12) United States Patent
Kaufmann et al.

(10) Patent No.: US 8,962,312 B2
(45) Date of Patent: Feb. 24, 2015

(54) PRODUCTION HOST CELL LINES

(75) Inventors: Hitto Kaufmann, Ulm (DE); Lore Florin, Biberach (DE); Eric Becker, Hochdorf (DE); Joey M. Studts, Biberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 625 days.

(21) Appl. No.: 12/507,252

(22) Filed: Jul. 22, 2009

(65) Prior Publication Data

US 2010/0021911 A1    Jan. 28, 2010

(30) Foreign Application Priority Data

Jul. 23, 2008 (EP) .................................. 08161030
Sep. 10, 2008 (EP) .................................. 08164054

(51) Int. Cl.
*C12N 15/85* (2006.01)
*C12P 21/02* (2006.01)
*C07K 16/00* (2006.01)
*C12N 9/06* (2006.01)
*C12N 15/63* (2006.01)

(52) U.S. Cl.
CPC .................. *C12P 21/02* (2013.01); *C07K 16/00* (2013.01); *C12N 9/003* (2013.01)
USPC .......................... 435/325; 435/320.1; 435/455

(58) Field of Classification Search
None
See application file for complete search history.

(56) References Cited

U.S. PATENT DOCUMENTS

| | | | |
|---|---|---|---|
| 5,776,746 A * | 7/1998 | Denney, Jr. .................... | 435/464 |
| 6,221,675 B1 | 4/2001 | Hauptmann et al. | |
| 8,535,940 B2 | 9/2013 | Kaufmann et al. | |
| 2003/0219871 A1 | 11/2003 | Enenkel et al. | |

FOREIGN PATENT DOCUMENTS

| | | |
|---|---|---|
| EP | 0393438 A2 | 10/1990 |
| EP | 1348758 A1 | 10/2003 |
| EP | 1953222 A1 | 8/2008 |

OTHER PUBLICATIONS

Eastman et al. (PNAS, 1991. vol. 88, pp. 8572-8576).*
International Search Report for PCT/EP2008/050699 mailed on Jul. 21, 2008.
Meents, Heiko, et al; Impact of Coexpression and Coamplification of sICAM and Antiapoptosis Determinants bcl-21 bcl-xL on Productivity, Cell Survival, and Mitochondria No. in CHO-DG44 Grown in Suspension and Serum-Free Media; Biotechnology and Bioengineering (2002) vol. 80, No. 6 pp. 706-716.
Meents, Heiko, et al; Amplified Dicistronic Expression Units Mediate Apoptosis Protection in CHO-DG44 Cells Adapted for Growth in Serum-Free Media, Impact on Mitochondria Copy Number; Animal Cell Technology Meets Genomics. Proceedings of the Esact Meeting (2003) vol. 2 pp. 115-120.
Chrast, Roman et al. "Linearization and purification of BAC DNA for the development of transgenic mice" Transgenic Research, 8: 147-150 (1999).
Eastman, Helen B., et al. "Stimulation of dihydrofolate reductase promoter activity by anitmetabolic drugs" Proc. Natl. Acad. Sci., vol. 88, 8572-8576, Oct. 1991.
International Search Report for PCT/EP2009/059400 mailed Oct. 6, 2009.
Lee, Moon Sue, et al. "Proteome Analysis of Antibody-Expressing CHO Cells in Response to Hyperosmotic Pressure" Biotechnology Progress, vol. 19, 1734-1741 (2003).
Wurm, Florian M, et al. "Gene transfer and gene amplification in mammalian cells" S.C. Makrides (Ed.) Elsevier Science B.V., Ch 7, pp. 309-335 (2003).
Dyring, Charlotte et al. "Stable, recombinant expression of human insulin-like growth factor binding protein-1 (hIGFBP-1) in Chinese hamster ovary (CHO) cells" Cytotechnology (1997) vol. 24, pp. 193-200.
US 5,843,791, 12/1998, Hauptmann (withdrawn)

* cited by examiner

*Primary Examiner* — Celine Qian
(74) *Attorney, Agent, or Firm* — Michael P. Morris; Edouard G. Lebel; Usha R. Patel

(57) ABSTRACT

The invention concerns the field of cell culture technology. The invention describes production host cell lines comprising vector constructs comprising a DHFR expression cassette. Those cell lines have improved growth characteristics in comparison to DHFR-deficient or DHFR-reduced cell lines such as CHO DG44 and CHO DUKX-B11. The invention especially concerns two cell lines, a representative of each cell line is deposited with the DSMZ under the number DSM ACC2909 (CHOpper® Discovery) and DSM ACC2910 (CHOpper® Standard). The invention further concerns a method of producing proteins using the cells generated by the described method.

13 Claims, 11 Drawing Sheets

A

B

| cell line | growth rate [1/d] | doubling time [h] |
|---|---|---|
| CHO wt | 0,92 | 18,2 |
| DG44 | 0,74 | 22,5 |
| CHOpper Discovery | 1,02 | 16,4 |

A

B

SEQUENCE LISTING

<160> NUMBER OF SEQ ID NOS: 10

<210> SEQ ID NO 1
<211> LENGTH: 21
<212> TYPE: DNA
<213> ORGANISM: Artificial
<220> FEATURE:
<223> OTHER INFORMATION: Primer dhfr (sense)

<400> SEQUENCE: 1
atggttcgac cgctgaactg c                                              21

<210> SEQ ID NO 2
<211> LENGTH: 23
<212> TYPE: DNA
<213> ORGANISM: Artificial
<220> FEATURE:
<223> OTHER INFORMATION: Primer dhfr (anti-sense)

<400> SEQUENCE: 2
ccactgagga ggtggtggtc att                                            23

<210> SEQ ID NO 3
<211> LENGTH: 21
<212> TYPE: DNA
<213> ORGANISM: Artificial
<220> FEATURE:
<223> OTHER INFORMATION: Primer tubulin (sense)

<400> SEQUENCE: 3
ctcaacgccg acctgcgcaa g                                              21

<210> SEQ ID NO 4
<211> LENGTH: 20
<212> TYPE: DNA
<213> ORGANISM: Artificial
<220> FEATURE:
<223> OTHER INFORMATION: Primer tubulin (anti-sense)

<400> SEQUENCE: 4
actcgctggt gtaccagtgc                                                20

<210> SEQ ID NO 5
<211> LENGTH: 2341
<212> TYPE: DNA
<213> ORGANISM: Artificial
<220> FEATURE:
<223> OTHER INFORMATION: dhfr expression cassette

<400> SEQUENCE: 5
tcagggaact gaggttaaaa gatgtatcct ggacctgcca gacctggcca ttcacgtaaa      60
cagaagattc cgcctcaagt tccggttaac aacaggaggc aacgagatct caaatctatt    120
acttctaatc gggtaattaa aaccttttcaa ctaaaacacg acccacgga tgtcacccac    180 ttttccttcc ccggctccgc cccttctcag tactccccac cattaggctc gctactctac    240
ctccacttcc gggcgcgaca cccacgtgcc ctctcccacc cgacgctaac cccgcccctg    300
cccgtctgac cccgcccacc acctggcccc gccccgttga ggacagaaga aaccccgggc    360
agccgcagcc aaggcggagc ggtagacgct gggggcgctg aggagtcgtc ctctaccttc    420
tctgctggct cggtgggga cgcggtggat ctcaggcttc ggaagactg gaagaaccgg    480 ctcagaaccg cttgtctccg cggggcttgg gcggcggaag aatggccgct agacgcggac    540
ttggtgcgag gcatcgcagg atgcagaaga gcaagcccgc cgggagcgcg cggctgtact    600

```
accccgcgcc tgcgagcgcg cacgccgcga ctgggcgggg ccggcctggt ggaggcggag    660
tctgacctcg tggaggcggg gcctctgatg ttcaaatagg atgctaggct tgttgagggc    720
gtggcctccg attcacaagt gggaagcagc ccgggcgact gcaatttcgc gccaaacttg    780
ggggaagcac agcgtacagg ctgcctaggt gatcgctgct gctgtcatgg ttcgaccgct    840
gaactgcatc gtcgccgtgt cccagaatat gggcatcggc aagaacggag accttccctg    900
gccaatgctc aggtactggc tggattgggt tagggaaacc gaggcggttc gctgaatcgg    960
gtcgagcact ggcggagac gcgcgggcca actacttagg acagtcatg aggggtaggc     1020
ccgccggctg ctgcccttgc ccatgccgc ggtgatcccc atgctgtgcc agcctttgcc    1080
cagaggcgct ctagctggga gcaaagtccg gtcactgggc agcaccaccc cccggacttg    1140
catgggtagc cgctgagatg gagcctgagc acacgtgaca gggtccctgt taacgcagtg    1200
tttctctaac tttcaggaac gagttcaagt acttccaaag aatgaccacc acctcctcag    1260
tggaaggtaa acagaacctg gtgattatgg gccggaaaac ctggttctcc attcctgaga    1320
agaatcgacc tttaaaggac agaattaata tagttctcag tagagagctc aaggaaccac    1380
cacaaggagc tcatttcctt gccaaaagtc tggacgatgc cttaaaactt attgaacaac    1440
cagagttagc agataaagtg gacatggttt ggatagttgg aggcagttcc gtttacaagg    1500
aagccatgaa tcagccaggc catctcagac tctttgtgac aaggatcatg caggaatttg    1560
aaagtgacac gttcttccca gaaattgatt tggagaaata taaacttctc ccagagtacc    1620
cagggggtcct ttctgaagtc caggaggaaa aaggcatcaa gtataaattt gaagtctatg    1680
agaagaaagg ctaacagaaa gatacttgct gattgacttc aagttctact gctttcctcc    1740
taaaattatg cattttaca agaccatggg acttgtgttg gctttagatc ctgtgcatcc    1800
tgggcaactg ttgtactcta agccactccc caaagtcatg ccccagcccc tgtataattc    1860
taaacaatta gaattatttt catttcatt agtctaacca ggttatatta aatatacttt    1920
aagaaacacc atttgccata aagttctcaa tgccctccc atgcagcctc aagtggctcc    1980
ccagcagatg catagggtag tgtgtgtaca agagacccca aagacataga gcccctgaga    2040
gcatgagctg atatgggggc tcatagagat aggagctaga tgaataagta caagggcag    2100
aaatgggttt taaacagcag agctagaact cagactttaa agaaaattag atcaaagtag    2160
agactgaatt attctgcaca tcagactctg agcagagttc tgttcactca gacagaaaat    2220
gggtaaattg agagctggct ccattgtgct ccttagagat gggagcaggt ggaggattat    2280
ataaggtctg gaacatttaa cttctccgtt tctcatcttc agtgagattc caagggatac    2340
t                                                                   2341

<210> SEQ ID NO 6
<211> LENGTH: 22
<212> TYPE: DNA
<213> ORGANISM: Artificial
<220> FEATURE:
<223> OTHER INFORMATION: Primer CMV for

<400> SEQUENCE: 6
ggcgtggata gcggtttgac tc                                              22

<210> SEQ ID NO 7
<211> LENGTH: 23
<212> TYPE: DNA
<213> ORGANISM: Artificial
<220> FEATURE:
```

```
<223> OTHER INFORMATION: Primer Terminator rev

<400> SEQUENCE: 7
accaccctgc catcccacaa cag                                    23

<210> SEQ ID NO 8
<211> LENGTH: 24
<212> TYPE: DNA
<213> ORGANISM: Artificial
<220> FEATURE:
<223> OTHER INFORMATION: Primer DHFR for-A

<400> SEQUENCE: 8
ctgctttcct cctaaaatta tgca                                   24

<210> SEQ ID NO 9
<211> LENGTH: 20
<212> TYPE: DNA
<213> ORGANISM: Artificial
<220> FEATURE:
<223> OTHER INFORMATION: Primer DHFR for-B

<400> SEQUENCE: 9
ccattgtgct ccttagagat                                        20

<210> SEQ ID NO 10
<211> LENGTH: 22
<212> TYPE: DNA
<213> ORGANISM: Artificial
<220> FEATURE:
<223> OTHER INFORMATION: Primer SV40 rev

<400> SEQUENCE: 10
cctcctcact acttctggaa ta                                     22
```

PRODUCTION HOST CELL LINES

This application claims priority benefit from EP 08161030.5, filed Jul. 23, 2008 and from EP 08164054.2, filed Sep. 10, 2008, which are incorporated herein in their entirety.

BACKGROUND OF THE INVENTION

1. Technical Field

The invention concerns the field of cell culture technology. It concerns production host cell lines containing vector constructs comprising a DHFR expression cassette. Those cell lines have improved growth characteristics in comparison to DHFR-deficient cell lines.

2. Background

The market for biopharmaceuticals for use in human therapy continues to grow at a high rate with over 900 biopharmaceuticals being evaluated in clinical studies and estimated sales of 50 billions in 2010. Over the years, an increasing number of biopharmaceuticals is produced from mammalian cells due to their ability to correctly process and modify human proteins. Successful and high yield production of biopharmaceuticals from mammalian cells is thus crucial and depends on the characteristics of the recombinant monoclonal cell line used in the process.

In biopharmaceutical production processes, yield is determined by two factors: the specific productivity ($P_{spec}$) of the host cell and the IVC, the integral of viable cells over time which produce the desired protein. This correlation is expressed by the following formula: $Y=P_{spec}*IVC$. Standard approaches to improve product yield therefore can be to increase either the production capacity of the host cell or viable cell densities in the bioreactor. One method to obtain higher IVCs is to improve the growth characteristics of cells, that means to generate cells which grow faster and to higher maximal cell densities.

The enzyme dihydrofolate reductase (DHFR) is one of the key enzymes of nucleotide synthesis. It catalyzes the reduction of di-hydrofolat to tetra-hydrofolat, a universal transmitter of C1-units in the synthesis of purin building blocks and of other metabolic pathways.

In biopharmaceutical industry and in academic research DHFR is widely used as a selection and amplification marker for the selective growth of stably transfected cell lines. Since DHFR is a non-dominant marker, this system is only applicable in cells which lack endogenous DHFR activity. Hence, when in the 1980's dhfr-negative Chinese hamster ovary (CHO) cells, CHO-DG44 and CHO-DUKX (B11), became available, they rapidly advanced to the host cell system of choice and are today the worldwide most frequently used mammalian production platform in the biopharmaceutical industry.

SUMMARY OF THE INVENTION

However, in this application we show that even in hypoxanthine and thymidine (HT) supplemented medium, dhfr-deficient CHO cells grow markedly slower and to reduced maximal cell densities compared to parental CHO wild type cells.

This reduced growth capacity of dhfr-negative cells (such as the CHO-DG44 cells) or cells with a very low endogenous dhfr-level (e.g. or DUKX-B11) has a negative impact on multiple aspects of the biopharmaceutical production process by causing:

Prolonged generation times of cells, which results in prolonged time lines in cell line development Lower efficiency after single cell cloning and slower growth thereafter Longer timeframes during scale up, especially in the case of inocculum for a production fermenter at large scale Lower product yield per fermenter run.

Therefore, there exists a strong need to improve the growth characteristics of producer host cells, especially those with low or no endogenous DHFR expression such as CHO-DG44.

In the present application, we show that this growth defect can be completely rescued by introduction of a DHFR expression cassette.

Enhanced cell growth has a profound impact on multiple aspects of the biopharmaceutical production process:

Shorter generation times of cells, which results in prolonged time lines in cell line development;

Higher efficiency after single-cell cloning and slower growth thereafter;

Shorter timeframes during scale-up, especially in the case of inocculum for a large-scale bioreactor;

Higher product yield per fermentation time due to the proportional correlation between IVC and product yield. Conversely, a low IVCs cause lower yields and/or longer fermentation times.

Additionally, enhanced cell growth and thus higher IVC's during fermentation are clearly advantageous wherever high biomasses are required, e.g. in order to get high product yield in short-term fermentations, to harvest high cell numbers for isolation, purification or characterization of intracellular or cell-bound components or to shorten the timelines for cell line generation, single-cell cloning and culture up-scaling.

As a consequence of their unfavourable growth characteristics, cells with reduced or no DHFR expression are therefore only applicable for industrial manufacturing when used in combination with the DHFR selection-/amplification system which is based on the re-introduction of DHFR into previously DHFR-deficient cells.

The requirement to re-introduce DHFR as selection-/amplification system constitutes a limitation to the choice of a suitable selection marker. Commonly used selection markers such as the glutamine synthetase (GS) system, neomycin, puromycin, bleomycin and others can in these cells not be used but in combination with the DHFR system. This is particularly unfeasible in cases where dual selection (meaning selection with two selective agents at the same time) is detrimental to cell survival and recovery of stable transfectants, such as concomitant selection for GS and neomycin.

Commonly used vector constructs contain a single selection marker to select for stably transfected cells and to ensure plasmid maintenance under selective conditions. In cells with low or no DHFR expression, this one marker would either have to be DHFR—in order to restore cell growth—or the combination of DHFR plus a second resistance gene which however would mean an additional selective pressure burden for the cell.

Thus, in addition to the negative impact on the production process mentioned earlier, the growth defect of cells with no or low DHFR expression leads to:

requirement to re-introduce DHFR heterologously to restore growth diminished flexibility in the choice of the selection marker to be used for the gene-of-interest and creates a problem or technical hurdle for the use of the GS system or other selection markers.

In summary, there exists an urgent need for host cells, especially CHO host cells, with optimized growth properties.

Furthermore, there exists the need to engineer host cells with disctinct growth properties for specific industrial purposes.

In this invention, we describe a cell with no or low endogenous DHFR levels comprising at least two heterologous vector constructs, whereby A first vector construct comprises a DHFR expression cassette, which comprises:
(i) an upstream regulatory sequence including a DHFR promoter,
(ii) a DHFR minigene,
(iii) a polyadenylation signal,
whereby said first vector construct does not contain a gene of interest nor another expression cassette encoding a eukaryotic protein, and A second vector construct comprises a gene of interest and a selection and/or amplification marker other than DHFR.

The present invention furthermore describes a method for generating said cell lines and preferred uses of said cell lines. Improved cell growth is achieved in the present invention by the introduction of a DHFR expression cassette into production cells and several rounds of subsequent screening and selection production relevant screening formats to identify cells with optimal growth characteristics.

Surprisingly, heterologous introduction of DHFR does not only restore cell growth in DG44 cells, but CHOpper® cells grow even faster than wildtype CHO cells. These data are in agreement with markedly shortened doubling times in inoculum cultures (FIG. 3). CHOpper® cell lines can be described in general as cells with heterologous DHFR expression whereby DHFR does not function as selection and/or amplification marker for a gene of interest.

From all CHOpper® clones generated we selected in particular two novel monoclonal CHO-DG44 derived cell lines with improved growth characteristics. These two cell lines are deposited with the Deutsche Sammlung von Mikroorganismen and Zellkulturen GmbH (DSMZ), Inhoffenstr, 7 B, D-38124 Braunschweig:

the fastest growing cell line, a representative of which was deposited on May 29, 2008 with the DSMZ under the number DSM ACC2909, and which we call "CHOpper® Discovery", and a second cell line, a representative of which was deposited on May 29, 2008 with the DSMZ under the number DSM ACC2910, whose growth reflects the behaviour of producer cell lines generated by a standard cell line generation procedure and which we therefore call "CHOpper® Standard".

The present invention thus describes especially a cell line deposited with the DSMZ under the number DSM ACC2909 and another cell line deposited with the DSMZ under the number DSM ACC2910.

The cell line "deposited with the DSMZ under the number DSM ACC2909 (CHOpper® Discovery)" was selected for optimal growth, meaning short doubling time (17 hrs), maximal cell densities and IVC's in fed-batch production processes as well as high DHFR expression levels. This cell line grows faster and expresses more DHFR compared to wild-type CHO cells.

The cell line deposited with the DSMZ under the number DSM ACC2910 (CHOpper® Standard) was selected for having growth characteristics comparable to usually used CHO producer cell lines. It is a "mock" cell line not expressing protein but showing growth curves representative for typical production clones generated by use of the DHFR system and subsequent gene amplification using MTX. Hence, cells deposited with the DSMZ under the number DSM ACC2910 (CHOpper® Standard) represent the ideal model cell line for industrial purposes such as establishment of Host Cell Protein (HCP)-ELISA or HCP depletion procedures, as well as for research applications such as analysis of cell growth, metabolic profiling or proteomics applications.

Proteomic analysis of either lysates or cell culture supernatant of production cell lines holds the promise for a better understanding of cellular processes associated with high-level production. Furthermore, proteomics approaches might be applied to identify proteolytic activities in the production process, investigation of secreted factors which mediate the growth-promoting effect of feeder cells or conditioned medium. Another important aim is to analyse the spectrum and amount of host cell protein contaminants in different steps of the purification process. Yet another application for production cell proteomics is to identify marker proteins for different process phases or the determination of for example the optimal harvest time point.

However, proteomics from cell-free cell culture samples of production cells is hindered by the dominant presence of the recombinant protein product which is secreted by the producer cell. As shown on the silver gel in FIG. 8A, fresh culture medium does not contain proteins in detectable amounts. In comparison, a CHO-DG44 host cell line secretes a wide spectrum of different proteins which appear as faint bands in the silver gel. However, in CHO-DG44-derived antibody producer cell lines, the most prominent band at a molecular size of about 150 kDa represents the recombinant antibody product. Considering the requirement for further concentration of the medium prior to proteomic analysis, the antibody at these concentrations would prevent sufficient resolution of the cell proteome and as most prominent signal overshine low abundance proteins. This constitutes an urgent need for a mock cell line which per definition should bear all genetic elements present in a production cell line except for the product. Additionally, the mock cell line should exhibit the same growth characteristics as the production cells to be used as a prediction tool for process marker proteins. The cells deposited with the DSMZ under the number DSM ACC2910 (CHOpper® Standard) of the present invention were selected to fulfill all of these criteria, making it the ideal model cell line for proteomics approaches. Example 5 (FIG. 8B) shows a broad spectrum of different proteins present in the cell supernatant, which can be nicely separated by a mastergel generated using a 2D-DIGE approach. This allows for the detection of a multitude of different spots with sufficient resolution to be recognized by an automated software, annotated and picked for further analysis.

Compared to the parental CHO-DG44 cell line, both the cell line deposited with the DSMZ under the number DSM ACC2909 (CHOpper® Discovery) and the cell line deposited with the DSMZ under the number DSM ACC2910 (CHOpper® Standard) show improved growth characteristics. They integrate the advantages of the CHO-DG44 host cell line (being well characterized, FDA-approved, low risk of viral burden, high productivity, robustness, transfectability, growth in suspension in serum-free medium) with the new property of faster cell doubling and improved performance in production processes.

We show that the improved growth characteristics directly correlate with the level of DHFR expression in the cells ("gene-dose effect"). Wild type CHO cells express endogenous DHFR, whereas CHO DG44 cells completely lack DHFR transcripts. The cells of the cell line deposited with the DSMZ under the number DSM ACC2909 (CHOpper® Discovery) show DHFR expression levels which are even higher than those of wildtype cells, which is well in line with their growth properties during fermentation.

Cells deposited with the DSMZ under the number DSM ACC2910 (CHOpper® Standard) also express DHFR, but in lower levels compared to wild type CHO cells (FIG. 4).

The specific CHOpper® cell lines exemplary described in the present invention contain a DHFR expression cassette as depicted in FIG. 5A (SEQ ID NO:5) comprising an upstream regulatory sequences (825 bp) derived from the hamster DHFR gene including the DHFR promoter, a DHFR minigene, comprising exon 1, intron 1 and exon 2 of the hamster DHFR gene, and a TAA stop codon and 647 bp of the 3' untranslated region including polyadenylation signal.

The vector construct used for generation of the CHOpper® cell lines described in the present invention is shown in FIG. 5B and contains the following functional elements: Cytomegalovirus (CMV) enhancer/promoter, Multiple cloning site, Polyadenylation signal, DHFR expression cassette, Origin of replication, beta-lactamase expression cassette for Ampicillin-resistance in bacteria.

The level of DHFR expression as measured by real-time PCR shows for the cell line deposited with the DSMZ under the number DSM ACC2909 (CHOpper® Discovery): high DHFR expression, levels being higher than in wild type CHO cells; for the cell line deposited with the DSMZ under the number DSM ACC2910 (CHOpper® Standard): DHFR expression levels between those detected in CHO DG44 and CHO wild type cells.

Both CHOpper® cell lines described in the present invention have doubling times below 24 hrs in standard inoculum cultures and without using peptones or other growth-promoting medium additives. The doubling time of the cell line deposited with the DSMZ under the number DSM ACC2910 (CHOpper® Standard) is ~22 h, the doubling time of the cell line deposited with the DSMZ under the number DSM ACC2909 (CHOpper® Discovery) is even below 18 hours (~17 h)

Cells deposited with the DSMZ under the number DSM ACC2909 (CHOpper® Discovery) are ideal host cells for recombinant protein production. Particularly, due to their optimized growth and no further requirement of exogenous DHFR, they are very well suited for use of the GS system which in the literature has been described to provide higher basal levels of product expression compared to the DHFR system without need for further amplification.

Antibody concentrations in all cell pools from the cell line deposited with the DSMZ under the number DSM ACC2909 (CHOpper® Discovery) are significantly higher compared to the titers measured in stably transfected wild type cells, the average difference ranging from 2-4-fold (FIG. 6). Thus, cells deposited with the DSMZ under the number DSM ACC2909 (CHOpper® Discovery) are not only suited for use of the GS system for recombinant protein production but they also yield higher product titers than wild type CHO cells in a side-by-side comparison.

Both cell lines described in the present invention offer full flexibility in the choice of the selection/amplification system. They are particularly suited as host cells for the glutamine synthetase (GS)-selection/amplification system. They are also applicable for the use of selection and/or amplification system(s) such as adenosine deaminase (ADA), cytosine deaminase (CDA), puromycin, neomycin, bleomycin etc.

Moreover, due to their fast growth and the high cell densities in production processes, they can be used wherever high yields of recombinant protein are desired, e.g. for purification/structural analysis in research, or when large cell biomasses are required, e.g. for isolation/investigation of cellular components such as nucleic acids or proteins.

The present invention demonstrates the superior characteristics of production cell lines engineered from CHOpper® cell lines, especially from the cell line deposited with the DSMZ under the number DSM ACC2909 (CHOpper® Discovery). FIG. 9 demonstrates that using CHOpper® Discovery as host cell leads to significantly shortened timelines in the development of antibody producer cell pools. Most importantly, the specific productivities are not compromised by this approach but are comparable to those obtained with producer cells derived from classic DG44 host cells (specific productivities are comparable between the top three pools from both approaches). Thus, cells deposited with the DSMZ under the number DSM ACC2909 (CHOpper® Discovery) are not only suited for use of the GS system for recombinant antibody production but they also allow for a fast track cell line development program while yielding producer cell lines with specific productivities comparable to the classic DG44 program (after one single round of methotrexate-mediated amplification) in a side-by-side comparison.

FIG. 10 demonstrates the excellent growth properties of CHOpper® Discovery-derived producer cells which grow to high cell densities of up to nearly 20 mio. cells/ml and have IVCs of 40 or more after only 7 days in fed-batch cultures. In comparison, producer cells derived from the 'classic' CHO DG44 host cell line usually reach maximum peak cell densities between 8 to 13 mio cells/ml in this platform process without any optimization. The surprisingly favourable growth profile of CHOpper® Discovery-derived producer cells is for example seen in FIG. 10A. CHOpper® Discovery-based producer cell lines grow rapidly and reach peak cell densities of 20 mio. cells/ml after seven days. Correspondingly, the integral of viable cells (IVC; FIG. 10B) is surprisingly high in those processes, which is particularly favorable in production schemes aiming for short processes (of <15 days) and multiple harvests a week.

The present invention is not obvious from the prior art.

CHO cells were established for the study of somatic cell genetics in 1957 (PUCK, 1957). By mutagenesis of the original K1 cell line, Urlaub und Chasin developed DHFR-deficient "CHO DG44" cells (Urlaub and Chasin, 1980) which exhibited a homozygous deletion of the chromosomal dhfr-locus (Urlaub et al., 1983). The growth properties of this newly established cell line were not investigated by the authors.

CHO DG44 cells quickly became the method of choice for transfections which employed the use of expression vectors carrying a functional dhfr gene together with an expression cassette for the gene of interest (GOI). DHFR is a non-dominant selection marker and hence is best used in cells lacking DHFR. However, it has been shown to be also applicable in host cells containing endogenous DHFR activity, e.g. by selecting with a second dominant marker (Kaufman et al., 1986), or mutant or bacterial dhfr genes (Simonsen and Levinson, 1983; Asselbergs and Widmer, 1995).

Under selective conditions, heterologous DHFR expression enables transfected cells to survive and proliferate. It has not been shown, however, that DHFR confers a growth advantage independent of its function as a selection marker and under non-selective conditions.

The dhfr gene belongs to the amplification markers, allowing the co-amplification of foreign genes after treatment with the folat analog methothrexat (MTX) (Schimke et al., 1978; Alt et al., 1978; Pallavicini et al., 1990). There is conclusive evidence, that co-amplification of a GOI together with dhfr is not dependent on whether both genes are contained on the same plasmid (Kaufman and Sharp, 1982). Consequently, expression strategies for recombinant antibody production have been reported where either both antibody chains are located on the same DNA plasmid together with the dhfr gene (Page and Sydenham, 1991), in which only one chain is functionally coupled with a dhfr expression cassette (Fouser et al., 1992) or where dhfr is encoded on a separate, co-integrating plasmid (Wurm and Jordan, 2003).

There are reports indicating that structural linkage of the dhfr gene and the GOI on the same DNA plasmid is not a pre-requisite for co-amplification since different co-transfected DNA constructs tend to co-integrate into adjacent chromosomal loci (Wurm, F. M. and Jordan, M. 2003. Gene Transfer and Gene Amplification in Mammalian Cells. In: Gene Transfer and Expression in Mammalian Cells, ed. S.C.Makrides Elsevier Science B.V., 309-335). It is important to note, that also in this setting, DHFR serves as a selection and/or amplification marker for the foreign GOI which constitutes a functional linkage despite structural separation.

In contrast, the present invention is based on the observation that heterologous DHFR, besides its well-known function as selection-/amplification marker for a GOI, exerts a completely independent function in improving cell growth.

Interestingly, there are numerous reports linking high DHFR expression with reduced cell growth, thereby opposing the desirable effect of heterologous gene amplification. Previous studies with *Escherichia coli* and *Saccharomyces cerevisiae* demonstrated that amplified dhfr gene copy numbers were accompanied by a decrease in the specific growth rate. (Bailey et al, 1986). Gu et al. showed reduced growth rates in beta-galactosidase expressing CHO-DG44 cells after dhfr-gene amplification by MTX treatment (Gu et al, 1992). Similar data were presented by Pendse et al. using a viral transgene coupled to DHFR (Pendse et al, 1992). Notably, both studies did not include cells expressing DHFR alone which prevents to conclude about the individual contribution of the multiple transgenes used. Importantly, they only compared the growth characteristics of dhfr-expressing amplified and un-amplified cells. Untransfected CHO-DG44 were not included. Snapka et al. demonstrated a reduction in cell growth with increasing dhfr gene copy numbers in NIH3T3-derived cells (Snapka et al, 1997). Interestingly and in contrast to their suggested mechanism, they also showed another adherent cell line which grew to higher cell densities after MTX-mediated dhfr amplification. They attributed this effect to reduced contact inhibition—which is not relevant for cells growing in suspension.

Taken together, in the present invention it is demonstrated for the first time, that heterologous expression of DHFR leads to an improvement of growth characteristics in CHO cells, especially CHO DG44 and CHO DUXX-(B11) cells. This function of DHFR might also be used to enhance cellular growth rates in other dhfr-negative or dhfr-reduced cell lines.

Possible applications/uses for the growth optimized CHO cell lines described in the present invention include:
  processes for production of recombinant proteins, such as industrial manufacturing of biopharmaceuticals or production of proteins for diagnostic or research applications,
  production of recombinant proteins using selection and/or amplification systems other than DHFR (e.g. the glutamine synthetase (GS) system),
  production processes aiming for accumulation of high amounts of biomass, e.g. for isolation and/or characterization of cellular components (e.g. proteins, nucleic acids, organelles, membrane fractions) for research purposes,
  use as reference/"mock"/control cells with comparable growth characteristics in experiments, e.g. cell engineering approaches or proteomics studies,
  use as reference cell for establishment of industrial downstream purification procedures, e.g. quantification/depletion of host cell proteins (HCPs) and establishment of HCP-ELISA methods. For these purposes, the cell line deposited with the DSMZ under the number DSM ACC2910 (CHOpper® Standard) can be used as standard cell line with a growth profile representative for commonly used DHFR-based amplified producer cells without expressing a protein of interest and thus allowing for the detection/quantification of low-abundance proteins.
  use of fast-growing cells not producing a protein of interest for generation of conditioned medium or use as autologous feeder cells

Cell growth curve in fed-batch processes. Cells were grown in shake-flasks for 6 days and feeded every 24 hours from day 3 on. Viable cell counts were determined daily using the CEDEX system. The following cells were compared: Wild type CHO cells (-●-; n=4); dhfr-reduced DUX-B11 (-Δ-; n=2), two DG44 cell lines from different sources (-■-; n=4) and DG44 cell pools stably transfected with vectors harbouring the dhfr gene (-♦-, n=9). Each data points represents average cell counts per genotype. Error bars =standard deviations. A representative growth curve out of five independent experiments is shown.

Figure 2:
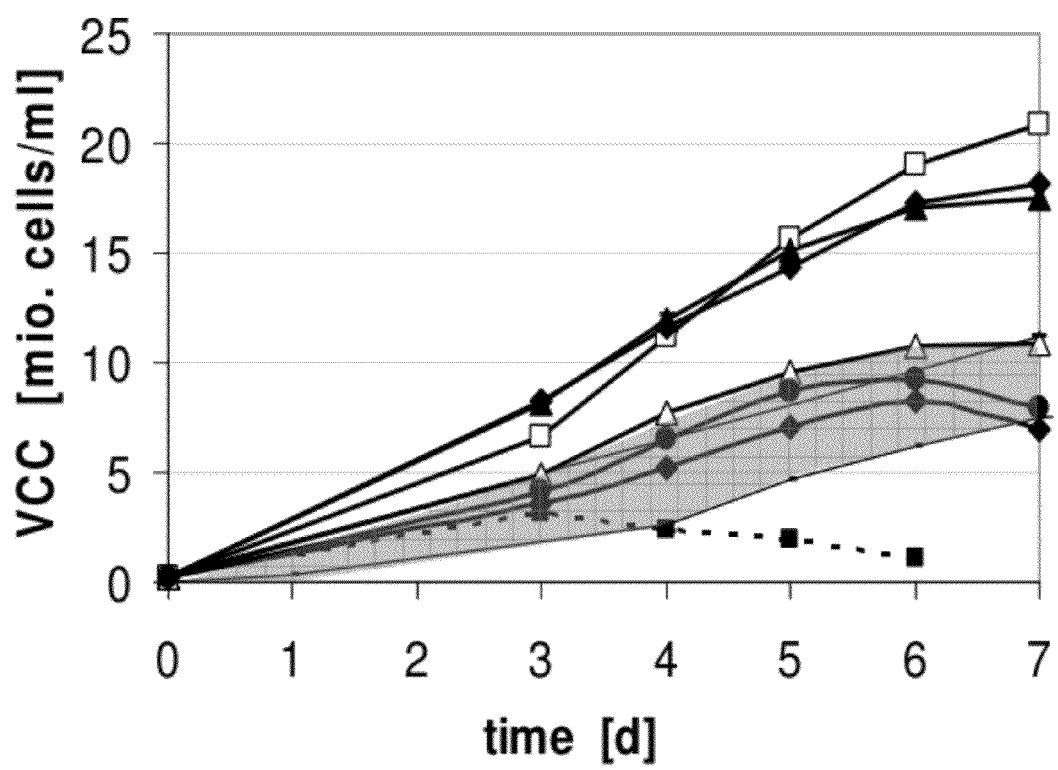

FIG. 2: Growth of Monoclonal CHOpper® Cell Lines During Fermentation

Figure 1:
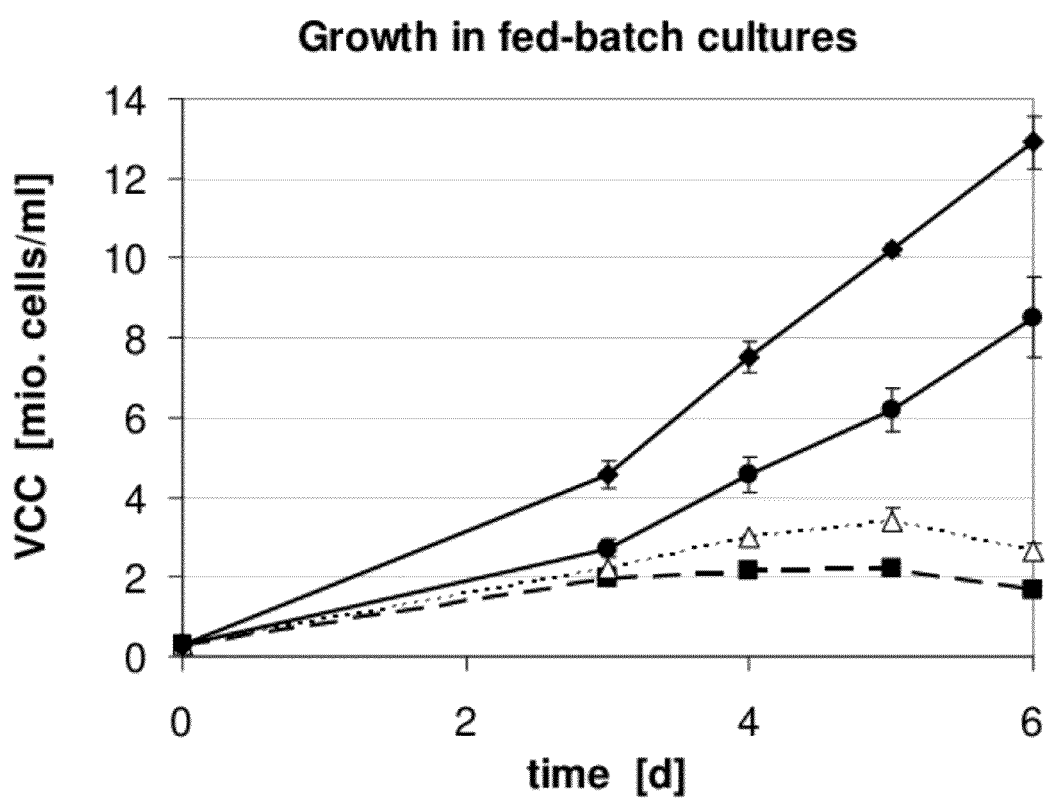
FIG. 1: Improved Growth by Heterologous DHFR

From the fastest growing DHFR-transfected DG44 cell population depicted in FIG. 1, monoclonal cell lines were generated using FACS-based single-cell cloning. Six CHOpper® clones (solid lines), the parental CHO-DG44 cell (-■-, dashed line) as well as three different producer cell clones expressing IgG1-type antibodies were included for comparison (n=3 each). Average cell numbers for each genotype were calculated and plotted with error bars representing standard deviations of the triplicates. The shaded area marks the difference between the fastest and the slowest growing production clone. The growth curves of the cell line deposited with the DSMZ under the number DSM ACC2909 (CHOpper® Discovery) and the cell line deposited with the DSMZ under the number DSM ACC2910 (CHOpper® Standard) are indicated by open squares and triangles, respectively.

Figure 3:
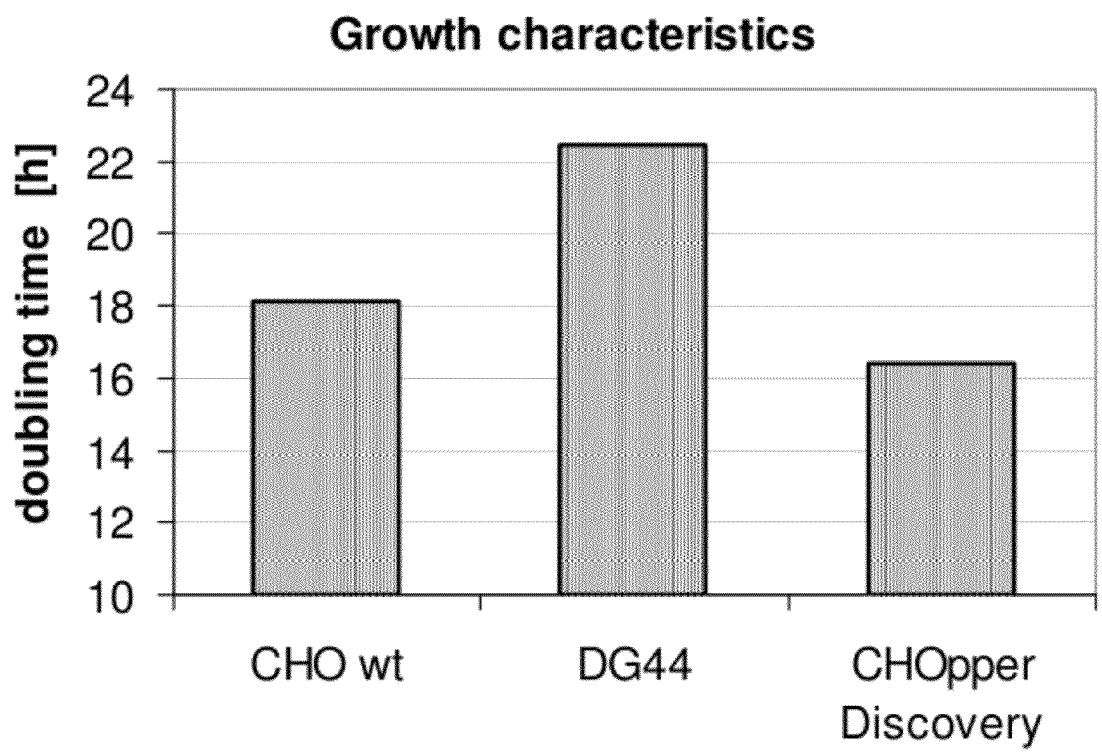

FIG. 3: Growth Properties of the Cell Line Deposited with the DSMZ Under the Number DSM ACC2909 (CHOpper® Discovery)

Growth characteristics during long-term cultivation. Cells were maintained at cell densities between 0.15-3xE06 cells/ml and splitted every 2-3 days during 8 passages. Growth rates and doubling times were calculated (B) and plotted (A) for wild type CHO, DG44 and the dhfr-transfected DG44 cell line deposited with the DSMZ under the number DSM ACC2909 (CHOpper® Discovery).

Figure 4:
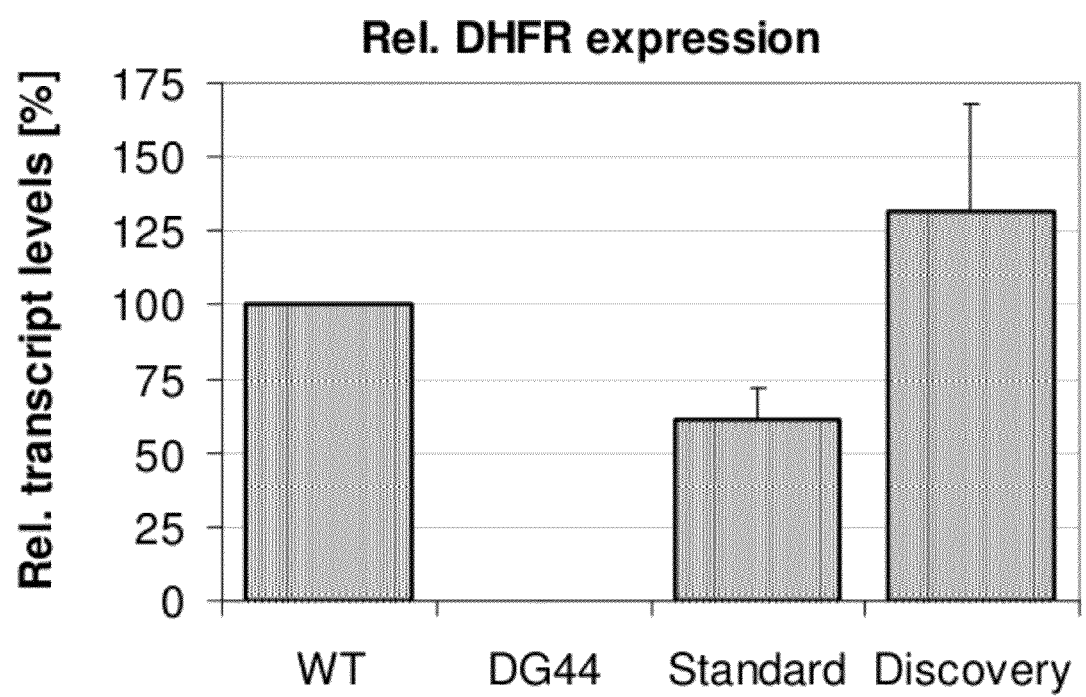

FIG. 4: Quantification of DHFR Expression

Total RNA was isolated from the above mentioned cells and quantitative real-time PCR was performed to determine DHFR-specific mRNA transcripts. Beta-tubulin mRNA levels were used for normalization.

Figure 5:
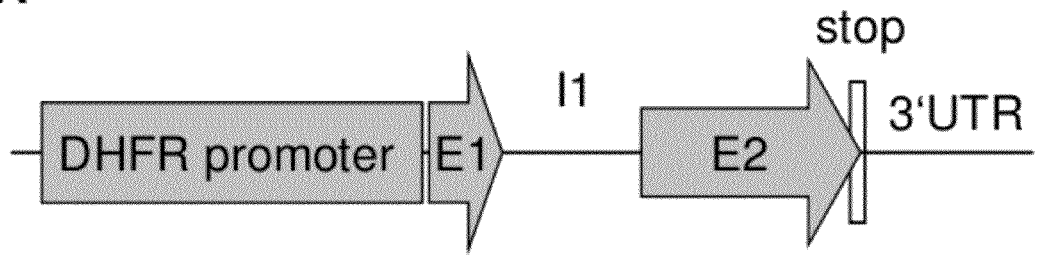
Figure 5:
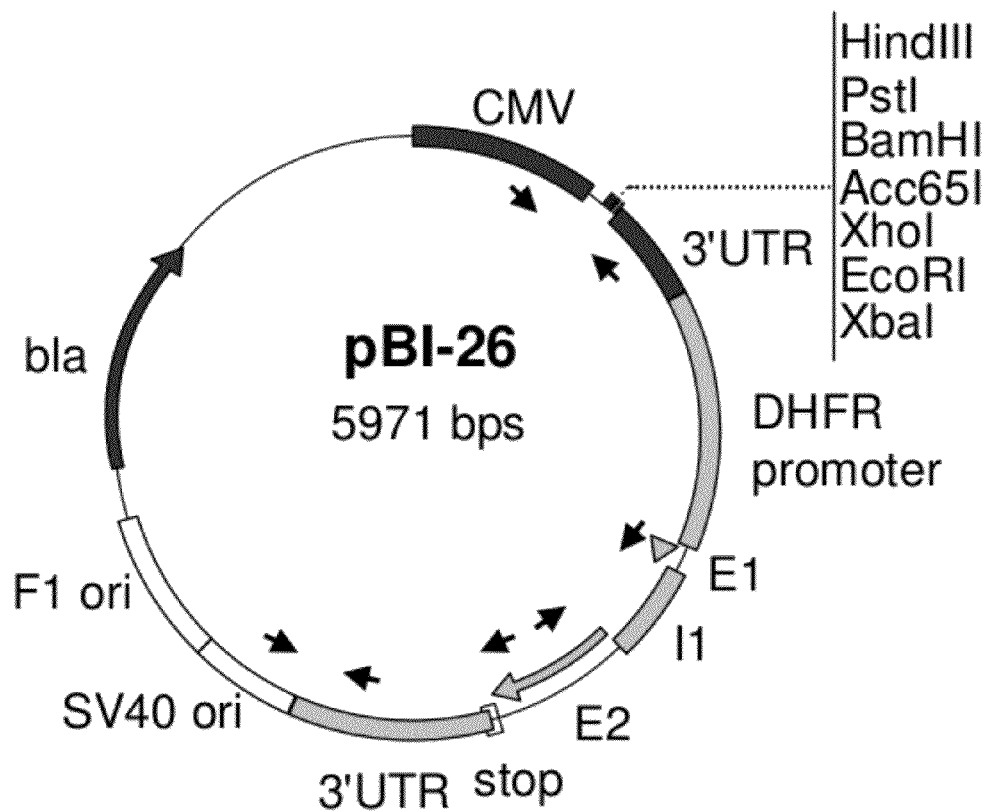

FIG. 5: Schematic Representation of the DHFR Expression Construct

A) Schematic representation of the DHFR expression cassette contained in the cell line deposited with the DSMZ under the number DSM ACC2909 (CHOpper® Discovery) and the cell line deposited with the DSMZ under the number DSM ACC2910 (CHOpper® Standard) cells. E1=Exon 1 of the hamster DHFR gene; I1=Intron 1; E2=Exon 2; Stop=TAA stop codon; 3'UTR=3' untranslated region.

B) Map of the vector construct transfected into CHO-DG44 cells to generate the CHOpper cells described in the present invention.

The plasmid was internally designated "pBI-26" and has a size of 5971 bp. Black arrowheads indicate binding positions of oligonucleotide primers suited for identification of the CHOpper® cell lines "Discovery" and "Standard". CMV=enhancer/promoter of the cytomegalovirus (CMV) early region, followed by a multiple cloning site (indicated by unique recognition sites for the indicated enzymes); F1 ori=origin for replication in bacteria; bla=beta-lactamase gene for ampicillin resistance.

Figure 6:
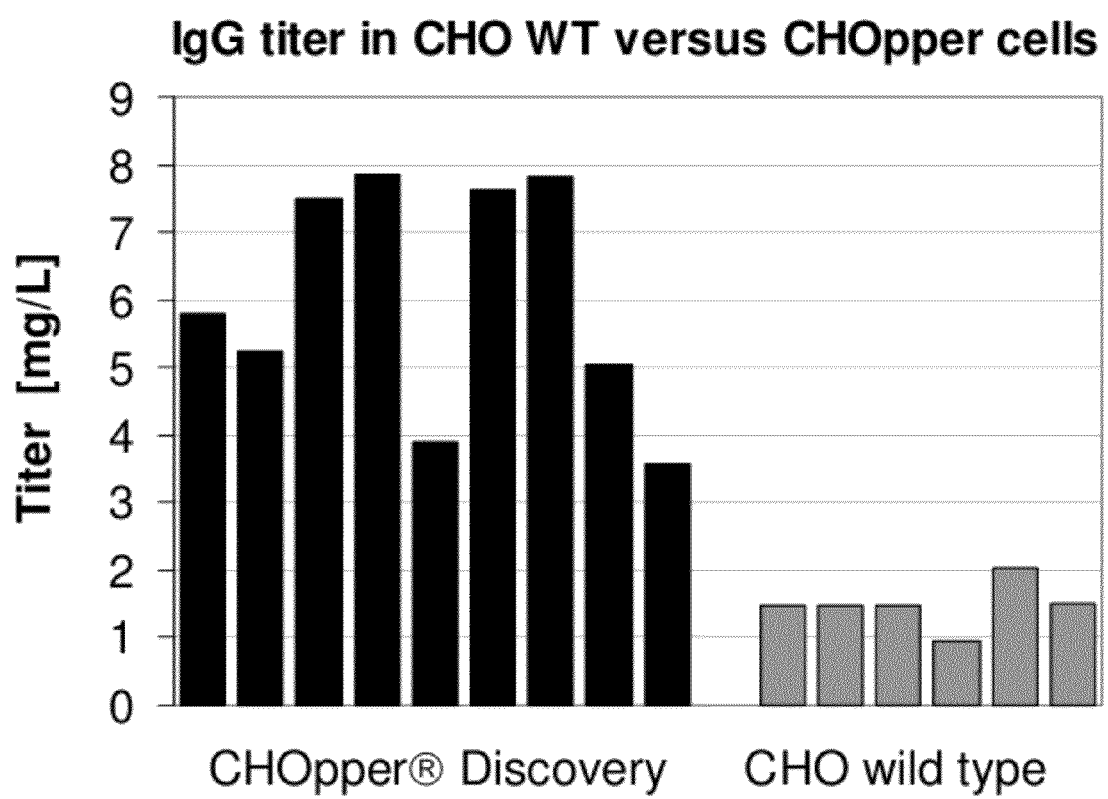

FIG. 6: Comparison of Antibody Titers/Protein Production Using the Glutamine Synthetase (GS) Selection System in Cells Deposited with the DSMZ Under the Number DSM ACC2909 (CHOpper® Discovery) in Comparison with CHO Wild Type Cells The cell line deposited with the DSMZ under the number DSM ACC2909 (CHOpper® Discovery) and CHO wild type cells were transfected with expression constructs encoding a human IgG1-type monoclonal antibody. Stable cell pools were generated using the glutamine synthetase (GS) system for selection. Antibody titers in cultures of IgG-producing cell pools from cells deposited with the DSMZ under the number DSM ACC2909 (CHOpper® Discovery) (black bars, n=9) and CHO wild type pools (grey bars, n=6) were determined during three consecutive passages. Average titers measured during three passages are plotted.

Figure 7:
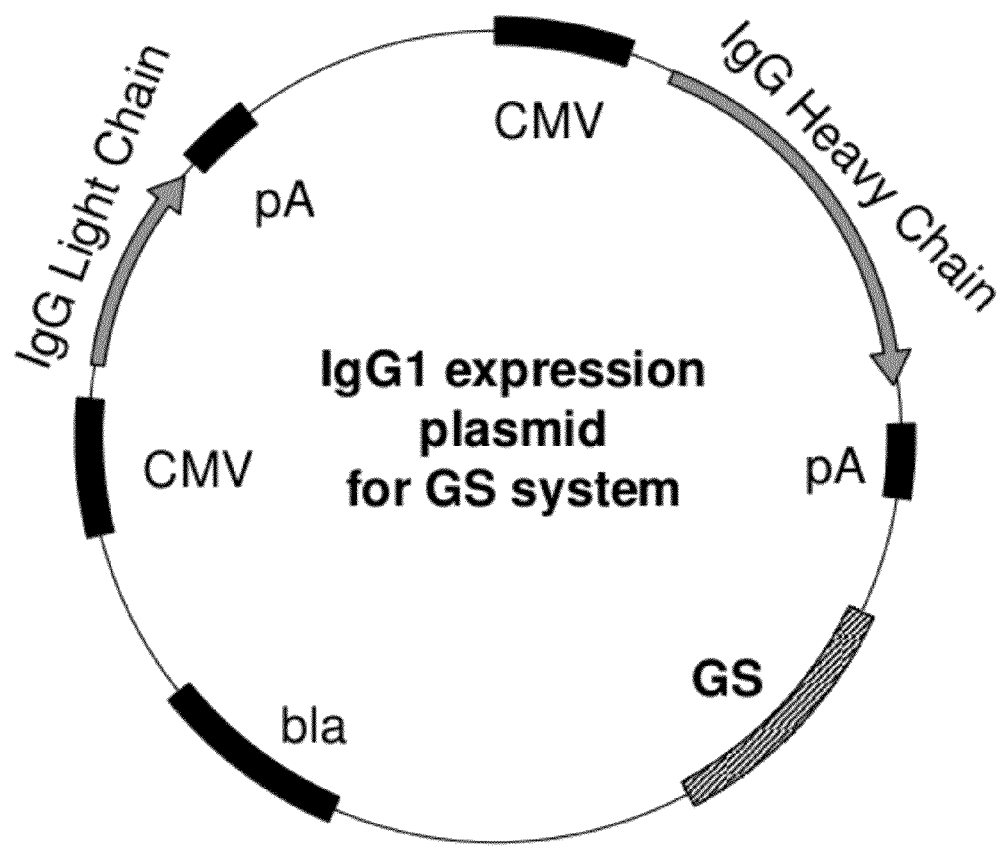

FIG. 7: Map of the Antibody Expression Construct

Expression construct for IgG1-type antibody production in CHOpper® and CHO wild type cell lines using the GS selection/amplification system The map depicts the IgG1 expression plasmid used for generation of the antibody-producing cell lines shown in FIG. 6. The vector contains genomic DNA sequences for both heavy and light chains of an IgG-type monoclonal antibody under control of the CMV promoter and the glutamine synthetase (GS) gene as marker gene for selection in the presence of MSX in glutamine-free medium. pA=polyadenylation signal; bla=beta lactamase gene for selection in bacteria.

Figure 8:
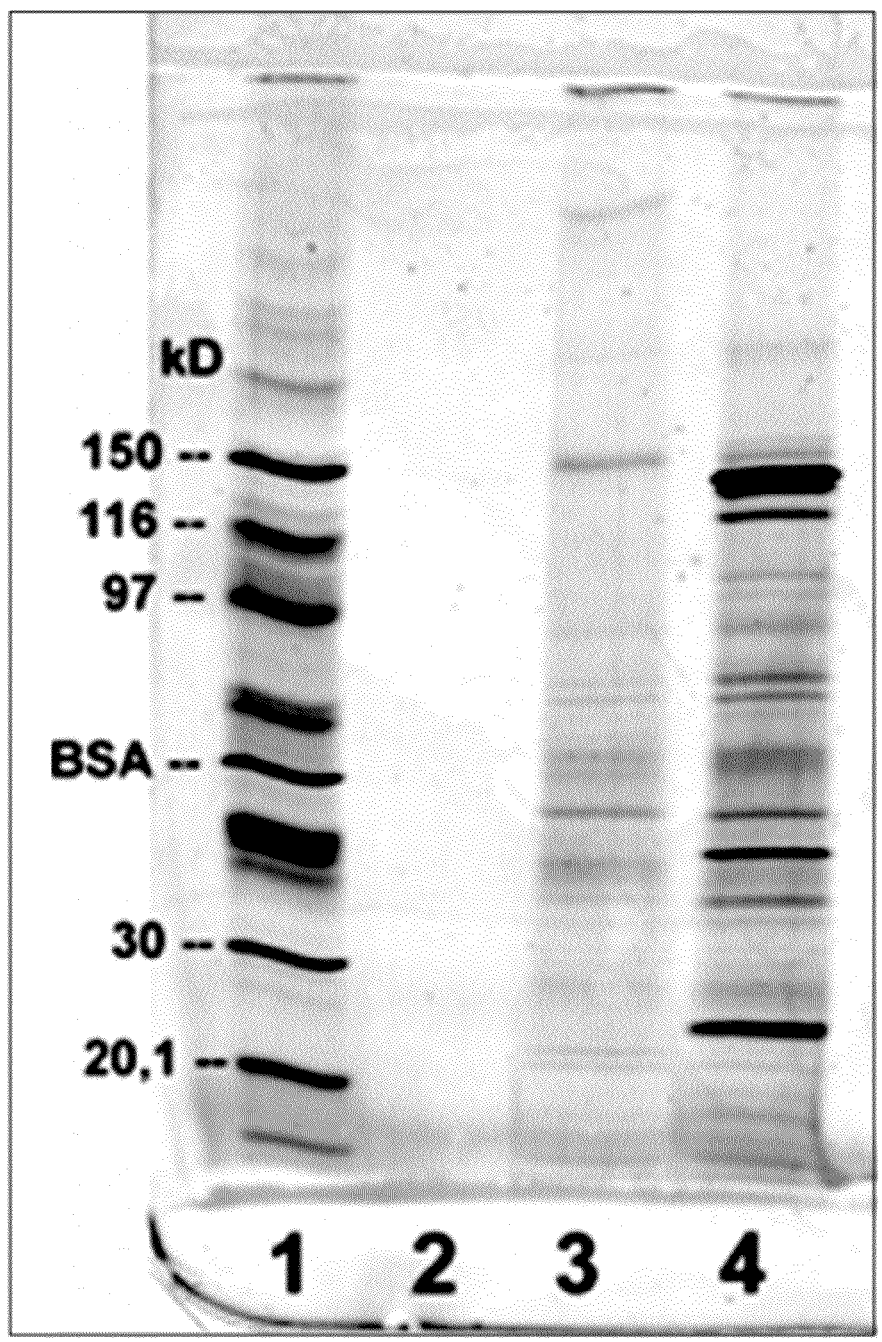
Figure 8:
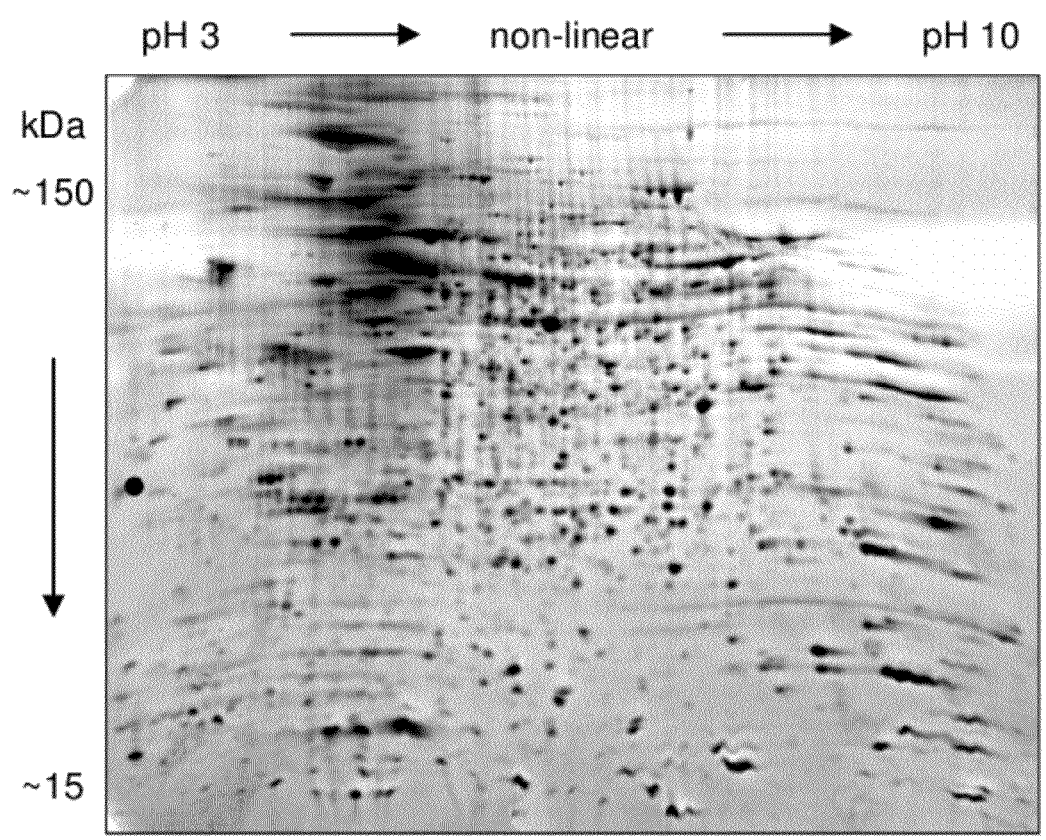

FIG. 8: Use of CHOpper® Standard as Reference Cell line for Proteomics (A) Silver-stained SDS-PAGE of molecular size marker (lane 1), fresh medium (lane 2) and samples of cell culture supernatent from untransfected CHO-DG44 cells (lane 3) and a DG-44-derived IgG1-producer cell line (lane 4). The most prominent band in the supernatant of producer cell lines at ~150 kDa represents the recombinant antibody product.

(B) Preparative 2D-PAGE mastergel showing the proteins present in concentrated supernatant of a culture of CHOpper® Standard cells. The cell culture supernatant was concentrated and separated in two dimensions according to size (15-150 kDa) and charge (isoelectric focussing in a pH range from pH 3.0 to 10.0, non-linear). Numbers indicate individual protein spots that have been identified by mass spectrometry (MS) analysis.

Figure 9:
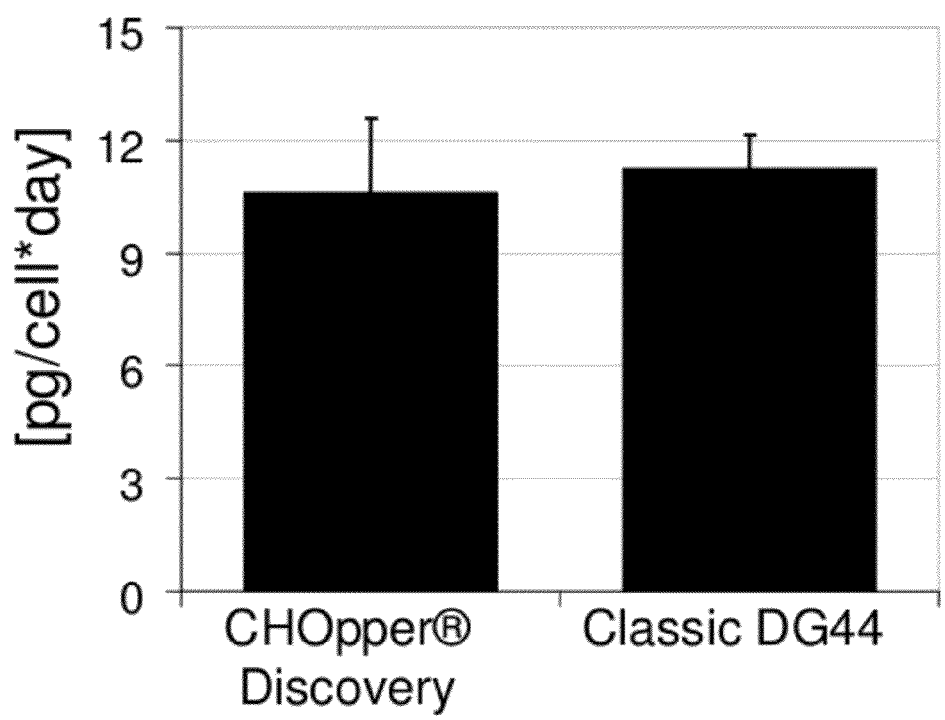

FIG. 9: Comparison of CHOpper™ Discovery and Classic DG44 Cells in Cell Line Development for an IGG1 Product—MAB1

Two cell line development projects were run side-by-side with either CHOpper® Discovery cells (using the GS-system for selection) or CHO DG44 host cells (using DHFR for selection). The table summarizes the comparison of timelines until end of pool phase and specific IgG1 productivities (Qp) of the top three pools at this stage. Development of MAB1 producer cells originating from CHOpper® Discovery cells is faster and allows to reduce timelines by about one month compared to the classic DG44 timeline without negative impact on the specific productivities which are comparable between the top three pools from both approaches. The diagram shows the mean Qp of the top three pools derived from CHOpper® Discovery and classic DG44 cells; error bars represents standard deviations.

Figure 10:
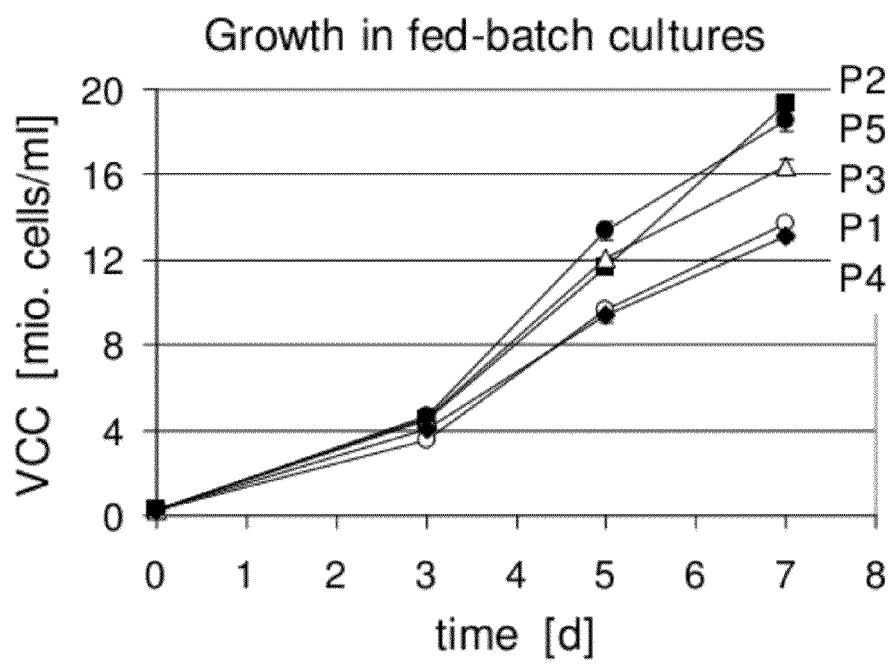
Figure 10:
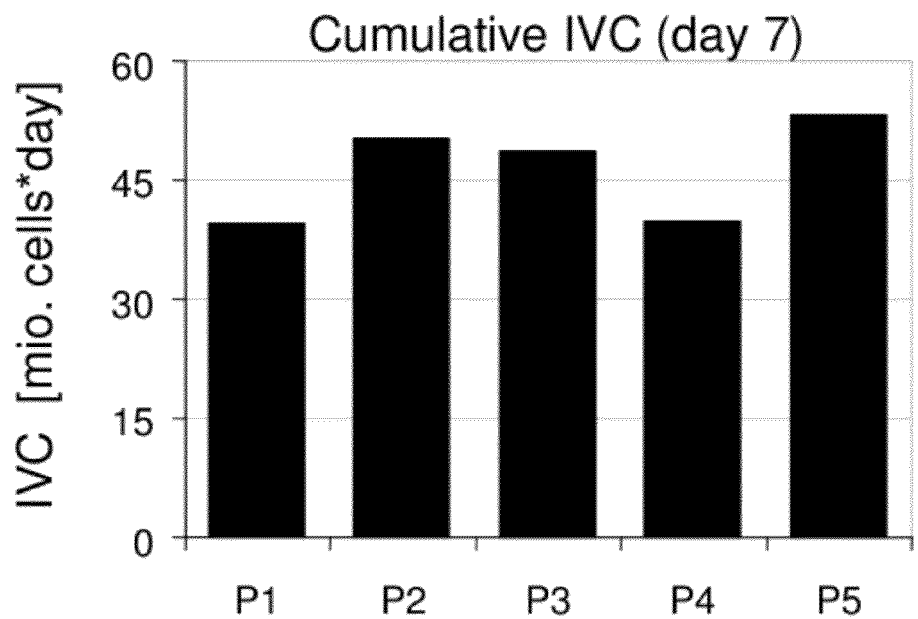

FIG. 10: Growth Characteristics for an IGG1 Production Cell Line—MAB2

(A) Growth curves of five IgG1-type antibody producing CHOpper® Discovery cell lines (P1-5) in a fed-batch process. Cells are seeded at 0.3 mio. cells/ml and grow to up to nearly 20 mio. cells/ml within seven days.

P1: open circles; P2: squares; P3: open triangles; P4: diamonds; P5: filled circles (B) IVCs of the same IgG1-type antibody producing CHOpper® Discovery cell lines shown in (A). The cumulative integral of viable cells over time (IVC) at day 7 of the fed-batch process is depicted for five cell pools (P1 to P5).

Both, high peak cell densities and cumulative IVCs demonstrate the excellent growth properties of CHOpper® Discovery-derived producer cell lines.

DETAILED DESCRIPTION OF THE INVENTION

The general embodiments "comprising" or "comprised" encompass the more specific embodiment "consisting of". Furthermore, singular and plural forms are not used in a limiting way.

Terms used in the course of this present invention have the following meaning.

The term "DHFR-deficient" means the same as "DHFR-negative". This describes cells with no DHFR expression, which means cells not functionally expressing the DHFR enzyme (e.g. CHO DG44). This can be caused by either
- homozygous deletion, which means that no gene copy is present at all or
- mutation of the DHFR gene, which means that the gene is present but altered in a way that no functional DHFR enzyme can be expressed at all.

Accordingly, a cell with no endogenous DHFR level is a DHFR-negative or DHFR-deficient cell and vice versa a DHFR-negative or DHFR-deficient cell is a cell with no endogenous DHFR level.

The term "DHFR-reduced" means cells with low endogenous DHFR enzyme levels, e.g. cells heterozygous for the DHFR gene (e.g. CHO DUKX (B11), which has only one gene copy). Accordingly, a cell with low endogenous DHFR level is a DHFR-reduced cell and vice versa a DHFR-reduced cell is a cell with low endogenous DHFR level. In one aspect of the present invention low endogenous DHFR level means some endogenous DHFR level which is less than the endogenous DHFR level of a wild type CHO cell (e.g. a CHO-K1 cell). In one further aspect of the present invention low endogenous DHFR level means some endogenous DHFR level which is equal or less than the endogenous DHFR level of a CHO DUKX (B11) cell.

DHFR-deficiency or DHFR-reduction can be measured by the following assays:

Southern Blot of genomic DNA of cell using part or the entire DHFR gene as a probe. DHFR-deficiency is confirmed by absence of signal. Endogenous DHFR and heterologous DHFR expression (as in CHOpper® cell lines and producer cell lines expressing a gene of interest functionally linked to a DHFR selection marker) can be distinguished by the individual band pattern ("finger print") as a result of different sites of genomic integration.

Fluorescence in situ hybridization (FISH) to detect and visualize the number of DHFR gene copies contained on the cells chromosomes. In DHFR-deficient CHO-DG44 cells, no signal will be detectable in this assay, whereas DHFR-reduced cells will show a single signal on one chromosome, but not the second homologous chromosome.

PCR on genomic DNA using the oligonucleotide primer sets described in TABLE 3 can be used to distinguished between wild type and DHFR-deficient, DG44 producer cells and the two CHOpper® cell lines "Discovery" and "Standard".

Norther Blot or (semi-) quantitative RT-PCR to detect and quantify the amount of DHFR-specific transcript in the cell. In DHFR-deficient cells such as CHO-DG44 cells, this assay will reveal no DHFR mRNA expression (see for example in FIG. 4.)

Enzymatic assay where DHFR-activity can be measured by its binding of the fluorescently labeled inhibitory drug methotrexate (MTX). Cells deficient for DHFR will not incorporate the fluorescent dye in contrast to DHFR expressing cells.

The term "DHFR gene" or "dhfr" means any nucleic acid encoding an active dihydrofolate reductase protein. This includes genomic DHFR sequences containing one or more introns, cDNA sequences or so called "minigenes", comprising DHFR regulatory sequences and coding sequences together with or without introns.

The term "DHFR expression construct" means any nucleic acid capable of being introduced into a cell and being intracellularly translated into DHFR protein. This includes circular or linear DNA constructs, isolated mRNAs or viruses encoding the DHFR protein. Each DHFR expression construct contains at least one "DHFR expression cassette" as functional unit.

Structurally, a DHFR expression cassette usually comprises a regulatory sequence such as a promoter, coding sequences for the DHFR enzyme, and optionally a terminator sequence providing a polyadenylation signal for RNA stability.

The term "DHFR minigene" refers to a DHFR gene encoding a functional DHFR protein but not comprising the complete DHFR gene. In one preferred aspect of the present invention, the term DHFR minigene refers to a DHFR gene encoding a functional DHFR protein but not comprising the complete genomic DHFR gene. Compared to the wild type DHFR gene, a DHFR minigene consists of a reduced set of exons and introns. In one aspect of the present invention, the DHFR minigene comprises only the first two exons of the DHFR gene. This means, that it comprises exon 1 and exon 2 of the DHFR gene. In one further specific aspect of the present invention the DHFR minigene comprises exon 1, intron 1 and exon 2 of the DHFR gene. However, any other combination of exons and/or introns constituting a reduced set of exons and/or introns is encompassed by the term DHFR minigene. In a preferred aspect of the present invention the DHFR minigene sequence is of hamster origin, which means that the exons and/or introns of the DHFR minigene are derived from the hamster DHFR gene. However, any other DHFR sequence from any other species is generally encompassed by the term DHFR minigene, preferably mouse, rat, human.

The use of a DHFR minigene is advantageous. It is smaller in size than a complete DHFR gene. Therefore, there are less recombination problems with the vector construct, it results in better transfection rates of the cells and the protein biosynthesis apparatus of the cell does not have to waste precious resources for the production of a complete or nearly complete DHFR enzyme. This is especially important in biopharmaceutical production, where it is advantageous to achieve very high titers/expression levels of the product/protein of interest. The use of a DHFR minigene leaves more resources for the production of the protein of interest and thus allows higher titers/expression levels of the protein of interest.

The term "cell culture" means multiple cells cultivated in one container under conditions suitable for the growth of the cells.

The terms "seed stock culture" and "inoculum culture" both describe the routinely used cultivation scheme whereby cells are kept in a proliferative state and are sub-cultivated every two to three days.

The term "integral of viable cell concentration over time" (IVC) means the area below the growth curve of a cell plotted over time and is a commonly used parameter to describe the growth performance of cells, e.g. in production processes which run over several days to weeks.

"Host cells" in the meaning of the present invention are cells such as hamster cells, preferably BHK21, BHK TK⁻, CHO, CHO-K1, CHO-DUKX, CHO-DUKX B1, and CHO-DG44 cells or the derivatives/progenies of any of such cell line. Particularly preferred are CHO-DG44, CHO-DUKX, CHO-K1 and BHK21, and even more preferred CHO-DG44 and CHO-DUKX cells. In a further embodiment of the present invention host cells also mean murine myeloma cells, preferably NS0 and Sp2/0 cells or the derivatives/progenies of any of such cell line. Examples of murine and hamster cells which can be used in the meaning of this invention are also summarized in Table 1. However, derivatives/progenies of those cells, other mammalian cells, including but not limited to human, mice, rat, monkey, and rodent cell lines, or eukaryotic cells, including but not limited to yeast, insect and plant cells, can also be used in the meaning of this invention, particularly for the production of biopharmaceutical proteins.

TABLE 1

Eukaryotic production cell lines

| CELL LINE | ORDER NUMBER |
| --- | --- |
| NS0 | ECACC No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 (BHK-21 derivative) | ATCC CRL-8544 |
| CHO | ECACC No. 8505302 |
| CHO wild type | ECACC 00102307 |
| CHO-K1 | ATCC CCL-61 |
| CHO-DUKX (= CHO duk⁻, CHO/dhfr⁻) | ATCC CRL-9096 |
| CHO-DUKX B11 | ATCC CRL-9010 |
| CHO-DG44 | (Urlaub et al., 1983) |
| CHO Pro-5 | ATCC CRL-1781 |
| CHO-S | Invitrogen Cat No. 10743-029 |
| Lec13 | (Stanley P. et al, 1984). |
| V79 | ATCC CCC-93 |
| B14AF28-G3 | ATCC CCL-14 |
| HEK 293 | ATCC CRL-1573 |
| COS-7 | ATCC CRL-1651 |
| U266 | ATCC TIB-196 |

TABLE 1-continued

Eukaryotic production cell lines

| CELL LINE | ORDER NUMBER |
|---|---|
| HuNS1 | ATCC CRL-8644 |
| Per.C6 | (Fallaux, F.J. et al, 1998) |
| CHL | ECACC No. 87111906 |

Host cells are most preferred, when being established, adapted, and completely cultivated under serum free conditions, and optionally in media which are free of any protein/peptide of animal origin.

The term "protein" is used interchangeably with amino acid residue sequences or polypeptide and refers to polymers of amino acids of any length. These terms also include proteins that are post-translationally modified through reactions that include, but are not limited to, glycosylation, acetylation, phosphorylation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with like properties.

The expression vector having a gene of interest encoding a protein of interest may also contain a selectable amplifiable marker gene.

The term "selective conditions" refers to conditions which do not allow for the growth or survival of cells which do not contain a corresponding selection marker. Selective conditions may be generated by using a medium containing additives such as antibiotics or lacking essential growth components.

The term "selectable marker" or "selection marker" is used for markers, which allow the growth/survival of cells under selective conditions. In the example of the selectable marker puromycin N-acetyl transferase (PAC) only cells containing the PAC gene will survive in selective media containing the antibiotic puromycin.

The term "amplifiable marker" or "amplification marker" is used for genes, which are amplified (e.g. doublicated, triplicated, multiplied) in the presence of a selective agent or upon treatment with a selective agent (e.g. methotrexat (MTX)) leading to an increase in the gene copy number of the marker (e.g. DHFR) and the surrounding DNA regions.

The "selectable amplifiable marker gene" usually encodes an enzyme which is required for growth of eukaryotic cells under those conditions. For example, the selectable amplifiable marker gene may encode DHFR which gene is amplified when a host cell transfected therewith is grown in the presence of the selective agent, methotrexate (MTX). The non-limited exemplary selectable genes in Table 3 are also amplifiable marker genes, which can be used to carry out the present invention. For a review of the selectable amplifiable marker genes listed in Table 3, see Kaufman, Methods in Enzymology, 185:537-566 (1990), incorporated by reference. Accordingly, host cells genetically modified according to any method described herein are encompassed by this invention, wherein the selectable amplifiable marker gene encodes for a polypeptide having the function of dihydrofolate reductase (DHFR), glutamine synthetase, CAD, adenosine deaminase, adenylate deaminase, UMP synthetase, IMP 5'-dehydrogenase, xanthine guanine phosphoribosyl transferase, HGPRTase, thymidine kinase, thymidylate synthetase, P glycoprotein 170, ribonucleotide reductase, asparagine synthetase, arginosuccinate synthetase, ornithine decarboxylase, HMG CoA reductase, acetylglucosaminyl transferase, threonyl-tRNA synthetase or $Na^+K^+$-ATPase.

One particular selectable amplifiable marker gene is the gene encoding dihydrofolate reductase (DHFR) which is necessary for the biosynthesis of purines. Cells lacking the DHFR gene will not grow on medium lacking purines. The DHFR gene is therefore useful as a dominant selectable marker to select and amplify genes in such cells growing in medium lacking purines. The selection agent used in conjunction with a DHFR gene is methotrexate (MTX).

Another selection and/or amplification marker is the glutamine synthetase (GS) gene, which is herein also referred to as "GS system". The GS gene encodes the glutamine synthetase enzyme which is required for synthesis of the amino acid glutamine. Cells lacking the GS gene or expressing low endogenous GS levels will not grow in glutamine-free media. The GS gene is therefore useful as a dominant selectable marker to select and amplify genes in such cells growing in glutamine-free medium. The selection agent used in conjunction with the GS gene is methionine sulfoximine (MSX).

TABLE 2

Selectable amplifiable marker genes

| Selectable Amplifiable Marker Gene | Accession Number | Selection Agent |
|---|---|---|
| Dihydrofolate reductase | M19869 (hamster) E00236 (mouse) | Methotrexate (MTX) |
| Metallothionein | D10551 (hamster) M13003 (human) M11794 (rat) | Cadmium |
| CAD (Carbamoyl-phosphate synthetase:Aspartate transcarbamylase: Dihydroorotase) | M23652 (hamster) D78586 (human) | N-Phosphoacetyl-L-aspartate |
| Adenosine deaminase | K02567 (human) M10319 (mouse) | Xyl-A- or adenosine, 2' deoxycoformycin |
| AMP (adenylate) deaminase | D12775 (human) J02811 (rat) | Adenine, azaserine, coformycin |
| UMP synthase | J03626 (human) | 6-Azauridine, pyrazofuran |
| IMP 5' dehydrogenase | J04209 (hamster) J04208 (human) M33934 (mouse) | Mycophenolic acid |
| Xanthine-guanine phosphoribosyltransferase | X00221 (E. coli) | Mycophenolic acid with limiting xanthine |

TABLE 2-continued

Selectable amplifiable marker genes

| Selectable Amplifiable Marker Gene | Accession Number | Selection Agent |
| --- | --- | --- |
| Mutant HGPRTase or mutant thymidine kinase | J00060 (hamster) M13542, K02581 (human) J00423, M68489 (mouse) M63983 (rat) M36160 (herpesvirus) | Hypoxanthine, aminopterin, and thymidine (HAT) |
| Thymidylate synthetase | D00596 (human) M13019 (mouse) L12138 (rat) | 5-Fluorodeoxyuridine |
| P-glycoprotein 170 (MDR1) | AF016535 (human) J03398 (mouse) | Multiple drugs, e.g. adriamycin, vincristine, colchicine |
| Ribonucleotide reductase | M124223, K02927 (mouse) | Aphidicolin |
| Glutamine synthetase | AF150961 (hamster) U09114, M60803 (mouse) M29579 (rat) | Methionine sulfoximine (MSX) |
| Asparagine synthetase | M27838 (hamster) M27396 (human) U38940 (mouse) U07202 (rat) | β-Aspartyl hydroxamate, Albizziin, 5' Azacytidine |
| Argininosuccinate synthetase | X01630 (human) M31690 (mouse) M26198 (bovine) | Canavanine |
| Ornithine decarboxylase | M34158 (human) J03733 (mouse) M16982 (rat) | α-Difluoromethylornithine |
| HMG-CoA reductase | L00183, M12705 (hamster) M11058 (human) | Compactin |
| N-Acetylglucosaminyl transferase | M55621 (human) | Tunicamycin |
| Threonyl-tRNA synthetase | M63180 (human) | Borrelidin |
| Na$^+$K$^+$-ATPase | J05096 (human) M14511 (rat) | Ouabain |

The present invention is suitable to generate host cells for the production of biopharmaceutical polypeptides/proteins.

"Gene of interest" (GOI), "selected sequence", or "product gene" have the same meaning herein and refer to a polynucleotide sequence of any length that encodes a product of interest or "protein of interest", also mentioned by the term "desired product". The selected sequence can be full length or a truncated gene, a fusion or tagged gene, and can be a cDNA, a genomic DNA, or a DNA fragment, preferably, a cDNA. It can be the native sequence, i.e. naturally occurring form(s), or can be mutated or otherwise modified as desired. These modifications include codon optimizations to optimize codon usage in the selected host cell, humanization or tagging. The selected sequence can encode a secreted, cytoplasmic, nuclear, membrane bound or cell surface polypeptide. In a preferred embodiment of the invention, the gene of interest is not a bacterial selection or resistance marker or any other gene, which is used for propagation of a vector construct per se. Preferably the gene of interest encodes a protein of interest, preferably a therapeutic protein, preferably an antibody.

The "protein of interest" includes proteins, polypeptides, fragments thereof, peptides, all of which can be expressed in the selected host cell. Desired proteins can be for example antibodies, enzymes, cytokines, lymphokines, adhesion molecules, receptors and derivatives or fragments thereof, and any other polypeptides that can serve as agonists or antagonists and/or have therapeutic or diagnostic use. Examples for a desired protein/polypeptide are also given below.

In the case of more complex molecules such as monoclonal antibodies the GOI encodes one or both of the two antibody chains.

The "product of interest" may also be an antisense RNA.

Proteins of interest or desired proteins are those mentioned above. Especially, desired proteins/polypeptides or proteins of interest are for example, but not limited to insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosisfactor (TNF), such as TNF alpha and TNF beta, TNF gamma, TRAIL; G-CSF, GM-CSF, M-CSF, MCP-1 and VEGF. Also included is the production of erythropoietin or any other hormone growth factors. The method according to the invention can also be advantageously used for production of antibodies or fragments thereof. Such fragments include e.g. Fab fragments (Fragment antigen-binding=Fab). Fab fragments consist of the variable regions of both chains which are held together by the adjacent constant region. These may be formed by protease digestion, e.g. with papain, from conventional antibodies, but similar Fab fragments may also be produced in the mean time by genetic engineering. Further antibody fragments include F(ab')2 fragments, which may be prepared by proteolytic cleaving with pepsin.

The protein of interest is preferably recovered from the culture medium as a secreted polypeptide, or it can be recovered from host cell lysates if expressed without a secretory signal. It is necessary to purify the protein of interest from other recombinant proteins and host cell proteins in a way that substantially homogenous preparations of the protein of interest are obtained. As a first step, cells and/or particulate cell debris are removed from the culture medium or lysate. The product of interest thereafter is purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin such as DEAE. In general, methods teaching a skilled person how to purify a protein heterologous expressed by host cells, are well known in the art.

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilised. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv).

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucin-zipper domains. However, there are also strategies in which the interaction between the VH/VL regions of the scFv are used for the multimerisation (e.g. dia-, tri- and pentabodies). By diabody the skilled person means a bivalent homodimeric scFv derivative. The shortening of the Linker in an scFv molecule to 5-10 amino acids leads to the formation of homodimers in which an inter-chain VH/VL-superimposition takes place. Diabodies may additionally be stabilised by the incorporation of disulphide bridges.

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a Linker region.

By triabody the skilled person means a: trivalent homotrimeric scFv derivative. ScFv derivatives wherein VH-VL are fused directly without a linker sequence lead to the formation of trimers.

The skilled person will also be familiar with so-called miniantibodies which have a bi-, tri- or tetravalent structure and are derived from scFv. The multimerisation is carried out by di-, tri- or tetrameric coiled coil structures.

The person skilled in the art will also be familiar with polypeptide molecules which consist of one or more variable domains of the single-chain antibody derived from lamas or other animals from the family of camelidae. Furthermore, the person skilled in the art is aware of derivatives, variants and fragments of such camelidae antibodies. Such molecules are also referred to as "domain antibodies". Domain antibody variants include several of those variable domains which are covalently connected by a peptide linker.

To increase serum half-life, domain antibodies can be generated which are fused to a polypeptide moiety such as an antibody Fc-part or another protein present in the blood serum such as albumin.

By "scaffold proteins" a skilled person means any functional domain of a protein that is coupled by genetic cloning or by co-translational processes with another protein or part of a protein that has another function.

The term "endogenous" means naturally being contained in the cell or organism. An endogenous gene is accordingly a gene which is found in the genome of the un-manipulated wild type cell.

By definition any sequences or genes introduced into a host cell and the respective proteins encoded thereby are called "heterologous", "heterologous sequences", "heterologous genes", "transgenes" or "heterologous proteins" with respect to the host cell, even if the introduced sequence, gene or protein encoded thereby is identical to an endogenous sequence or gene or protein in the host cell.

Heterologous gene sequences can be introduced into a target cell by using an "expression vector"/"vector construct", preferably an eukaryotic, and even more preferably a mammalian expression vector/vector construct. Methods used to construct vectors are well known to a person skilled in the art and described in various publications. In particular techniques for constructing suitable vectors, including a description of the functional components such as promoters, enhancers, termination and polyadenylation signals, selection markers, origins of replication, and splicing signals, are known in the art. Vectors may include but are not limited to plasmid vectors, phagemids, cosmids, artificial/mini-chromosomes, or viral vectors such as baculovirus, retrovirus, adenovirus, adeno-associated virus, herpes simplex virus, retroviruses, bacteriophages. The eukaryotic expression vectors/vector constructs will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operatively linked, are well known in the art and some are commercially available from companies such as Stratagene, La Jolla, Calif.; Invitrogen, Carlsbad, Calif.; Promega, Madison, Wis. or BD Biosciences Clontech, Palo Alto, Calif.

In a preferred embodiment the expression vector/vector construct comprises at least one nucleic acid sequence which is a regulatory sequence necessary for transcription and translation of nucleotide sequences that encode for a peptide/polypeptide/protein of interest.

The term "expression" as used herein refers to transcription and/or translation of a heterologous nucleic acid sequence within a host cell. The level of expression of a desired product/protein of interest in a host cell may be determined on the basis of either the amount of corresponding mRNA that is present in the cell, or the amount of the desired polypeptide/protein of interest encoded by the selected sequence as in the present examples. For example, mRNA transcribed from a selected sequence can be quantitated by Northern blot hybridization, ribonuclease RNA protection, in situ hybridization to cellular RNA or by PCR. Proteins encoded by a selected sequence can be quantitated by various methods, e.g. by ELISA, by Western blotting, by radioimmunoassays, by immunoprecipitation, by assaying for the biological activity of the protein, by immunostaining of the protein followed by FACS analysis or by homogeneous time-resolved fluorescence (HTRF) assays.

"Transfection" of eukaryotic host cells with a polynucleotide or expression vector, resulting in genetically modified cells or transgenic cells, can be performed by any method well known in the art and described. Transfection methods include but are not limited to liposome-mediated transfection, calcium phosphate co-precipitation, electroporation, polycation (such as DEAE-dextran)-mediated transfection, protoplast fusion, viral infections and microinjection. Preferably, the transfection is a stable transfection. The transfection method that provides optimal transfection frequency and expression of the heterologous genes in the particular host cell line and type is favored. Suitable methods can be determined by routine procedures. For stable transfectants the constructs are either integrated into the host cell's genome or an artificial chromosome/mini-chromosome or located episomally so as to be stably maintained within the host cell.

Within the scope of the present description the terms "functional linking", "functionally linked" or "operably linked" means that two or more nucleic acid sequences or sequence elements are positioned in a way that permits them to function in their intended manner. For example, a selection/amplification marker is functionally or operably linked to a gene of interest, when the addition of the selecting agent to the cultivation medium (e.g. methotrexate in case of the DHFR marker) results in the selection of cells expressing said gene of interest. The selection/amplification marker is not functionally or operably linked, if it does not serve as selection marker for a gene of interest. Furthermore, for example, a promoter/enhancer is functionally linked to a coding gene sequence if it is able to control or modulate the transcription of the linked gene sequence in the cis position. Generally, but not necessarily, the DNA sequences that are functionally linked are contiguous and, where necessary to join two polypeptide coding regions or in the case of a secretion signal peptide, contiguous and in reading frame. However, although an operably linked promoter is generally located upstream of the coding sequence, it is not necessarily contiguous with it. Enhancers do not have to be contiguous as long as they increase the transcription of the coding sequence. For this they can be located upstream or downstream of the coding sequence and even at some distance. A polyadenylation site is operably linked to a coding sequence if it is located at the 3'end of the coding sequence in a way that transcription proceeds through the coding sequence into the polyadenylation signal. Linking is accomplished by recombinant methods known in the art, e.g. using PCR methodology, by ligation at suitable restrictions sites or by annealing. Synthetic oligonucleotide linkers or adaptors can be used in accord with conventional practice if suitable restriction sites are not present.

The term "intron" as used herein, refers to a non-coding nucleic acid sequence of varying length, normally present within many eukaryotic genes, which is removed from a newly transcribed mRNA precursor by the process of splicing for which highly conserved sequences at or near either end of the intron are necessary. In general, the process of splicing requires that the 5' and 3'ends of the intron be correctly cleaved and the resulting ends of the mRNA be accurately joined, such that a mature mRNA having the proper reading frame for protein synthesis is produced. Many splice donor and splice acceptors sites, meaning the sequences immediately surrounding the exon-intron- and intron-exon-boundaries, have been characterized and described and are known to the skilled artisan.

The term "production cell proteomics" as used in the present invention means the analysis of the sum of all proteins expressed in a cell, which is a producer host cell and/or which produces high amounts of a certain protein or product of interest. Such producer cells are used in the biopharmaceutical production process for the generation of recombinant proteins/polypeptides. Proteomics approaches can be used to identify proteins expressed in a cell or secreted from a cell, to compare the global protein abundance between different samples representing e.g. different species, different cell types or samples generated at different time points during a process such as a fermentation process. Furthermore, proteomics can be used to identify protein-protein interactions, protein modifications or for the search of marker proteins, meaning single proteins or protein patterns which are representative for a given state of the process or the cell under investigation. In industrial applications, production cell proteomics is used to analyse the proteomics differences between high- and low producer cell lines, to study growth factors in conditioned medium or to investigate and quantify the amount and nature of host cell proteins during downstream purification processes.

The practice of the present invention will employ, unless otherwise indicated, conventional techniques of cell biology, molecular biology, cell culture, immunology and the like which are in the skill of one in the art.

This invention relates to a cell with no or low endogenous DHFR levels comprising at least two heterologous vector constructs, whereby
(a) A first vector construct comprises a DHFR expression cassette, which comprises:
(i) an upstream regulatory sequence including a DHFR promoter,
(ii) a DHFR minigene,
(iii) a polyadenylation signal,
whereby said first vector construct does not contain a gene of interest nor another expression cassette encoding a eukaryotic protein, and
(b) A second vector construct comprises a gene of interest and a selection and/or amplification marker other than DHFR.

Preferably, the DHFR minigene comprises only the first two exons of the DHFR gene.

Preferably, the DHFR minigene comprises exon 1 and exon 2 of the DHFR gene. More preferably, the DHFR minigene comprises or consists essentially of or consists of exon 1, intron 1, and exon 2 of the DHFR gene. Most preferably, the DHFR minigene is derived from the hamster DHFR gene.

In a preferred embodiment of the invention, the gene of interest is not a bacterial selection or resistance marker or any other gene, which is used for propagation of a vector construct per se. Preferably the gene of interest encodes a protein of interest, preferably a therapeutic protein. In a specifically preferred embodiment of the invention the protein of interest is a secreted protein, e.g. an antibody. Particularly preferred is a synthetic protein or a fusion protein which is secreted. In a further preferred embodiment of the invention the selection marker on the second vector construct is glutamine synthetase (GS).

In another preferred embodiment of the invention the cell has improved properties. In one aspect of the present invention the cell has a higher DHFR expression than a wildtype cell and an IVC at day 5 in fed-batch culture which is at least 2-fold higher compared to the parental cell line.

In another aspect of the present invention the cell has a DHFR expression level higher than the parental cell and an IVC at day 5 in fed-batch culture which is comparable/within a range of ±30% to the IVC of an amplified monoclonal DHFR-based production cell line.

The invention specifically relates to a cell with no or low endogenous DHFR levels comprising at least two heterologous vector constructs, whereby:
(a) A first vector construct comprises as the only mammalian expression cassette in said first vector construct a DHFR expression cassette, which comprises:

(i) an upstream regulatory sequences including a DHFR promoter,
(ii) a DHFR minigene comprising exon 1, intron 1 and exon 2 of the hamster DHFR gene,
(iii) a polyadenylation signal, and
(b) A second vector construct comprises a gene of interest and a selection and/or amplification marker other than DHFR.

In a specific embodiment of the present invention said cell is characterized in that the vector constructs are stably integrated into the cells genome.

In another specific embodiment of the present invention said cell is characterized by a specific PCR band pattern/fingerprint when using genomic DNA as template, whereby:
(a) a 437 bp PCR product is generated using the oligonucleotide primers of SEQ ID NO: 1 and SEQ ID NO:2, and
(b) a 438 bp PCR product is generated using the oligonucleotide primers of SEQ ID NO: 6 and SEQ ID NO: 7, and
(c) a 928 bp PCR product is generated using the oligonucleotide primers of SEQ ID NO: 8 and SEQ ID NO: 10, and/or
(d) a 416 bp PCR product is generated using the oligonucleotide primers of SEQ ID NO: 9 and SEQ ID NO: 10.

In a preferred embodiment of the present invention said cell is characterized by a specific PCR band pattern/fingerprint when using genomic DNA as template, whereby:
(a) a 437 bp PCR product is generated using the oligonucleotide primers of SEQ ID NO: 1 and SEQ ID NO:2, and
(b) a 438 bp PCR product is generated using the oligonucleotide primers of SEQ ID NO: 6 and SEQ ID NO: 7, and
(c) a 928 bp PCR product is generated using the oligonucleotide primers of SEQ ID NO: 8 and SEQ ID NO: 10.

In another preferred embodiment of the present invention said cell is characterized by a specific PCR band pattern/fingerprint when using genomic DNA as template, whereby:
(a) a 437 bp PCR product is generated using the oligonucleotide primers of SEQ ID NO: 1 and SEQ ID NO:2, and
(b) a 438 bp PCR product is generated using the oligonucleotide primers of SEQ ID NO: 6 and SEQ ID NO: 7, and
(c) a 928 bp PCR product is generated using the oligonucleotide primers of SEQ ID NO: 9 and SEQ ID NO: 10.

The invention further relates to a cell with no or low endogenous DHFR levels comprising a vector construct containing a DHFR expression cassette which comprises
(a) An upstream regulatory sequences including a DHFR promoter,
(b) A DHFR minigene comprises exon 1, intron 1 and exon 2 of the hamster DHFR gene,
(c) A polyadenylation signal,
whereby the DHFR expression cassette is not functionally or operably linked as a selection and/or amplification marker to a gene of interest (GOI) encoding a protein of interest.

The invention furthermore relates to a cell with no or low endogenous DHFR levels comprising a vector construct containing a DHFR expression cassette which comprises
(a) An upstream regulatory sequences including a DHFR promoter,
(b) A DHFR minigene comprises exon 1, intron 1 and exon 2 of the hamster DHFR gene,
(c) A polyadenylation signal,
whereby the DHFR expression cassette is separated from the gene of interest by at least 0.5 kbp, 1 kbp, 2 kbp, 5 kbp or 10 kbp. Preferably the two elements are separated by more than 10 kbp. Preferably the two elements are separated by at least 1 kbp, more preferably by at least 5 kpb.

In a preferred embodiment of the present invention said cell is characterized in that said cell is a Chinese hamster ovary (CHO) cell, preferably a CHO cell with no endogenous DHFR levels such as CHO DG44 (described by Urlaub et al., 1983, Cell 33, 405-412).

In another preferred embodiment of the present invention said cell is characterized in that said cell is a CHO cell with low endogenous DHFR levels such as the cell deposited under the number ATCC CRL-9010 (CHO DUKX-B11).

In another preferred embodiment of the present invention said cell is characterized in that the cell is a cell, a representative of which is deposited with the Deutsche Sammlung von Mikroorganismen und Zellkulturen (DSMZ) GmbH (=German Collection of Microorganisms and Cell Cultures) under the number DSM ACC2909 or DSM ACC2910.

In a preferred embodiment of the present invention said cell is characterized in that the upstream regulatory sequences and the DHFR gene are both derived from hamster.

In a preferred embodiment of the present invention said cell is characterized in that the DHFR expression cassette consists of the SEQ ID NO: 5. The invention thus specifically relates to a cell with no or low endogenous DHFR levels comprising a vector construct comprising a DHFR expression cassette having the SEQ ID NO: 5, whereby the DHFR expression cassette is not functionally or operably linked as a selection and/or amplification marker to a gene of interest (GOI) encoding a protein of interest. The invention thus specifically relates to a cell with no or low endogenous DHFR levels comprising a vector construct comprising a DHFR expression cassette having the SEQ ID NO: 5, whereby the DHFR expression cassette is separated from a gene of interest by at least 0.5 kbp, 1 kbp, 2 kbp, 5 kbp or 10 kbp. Preferably the two elements are separated by more than 10 kbp. Preferably the two elements are separated by at least 1 kbp, more preferably by at least 5 kpb.

The invention thus specifically relates to a cell with no or low endogenous DHFR levels comprising at least two heterologous vector constructs, whereby
(a) A first vector construct comprises as the only mammalian expression cassette in said first vector construct a DHFR expression cassette having the SEQ ID NO: 5, and
(b) A second vector construct contains a gene of interest and a selection and/or amplification marker other than DHFR.

The invention furthermore specifically relates to a cell with no or low endogenous DHFR levels comprising at least two heterologous vector constructs, whereby
(a) A first vector construct comprises a DHFR expression cassette having the SEQ ID NO: 5, whereby said first vector construct does not contain a gene of interest nor another expression cassette encoding a eukaryotic protein, and
(b) A second vector construct comprises a gene of interest and a selection and/or amplification marker other than DHFR.

In another specific embodiment of the present invention the cell is characterized in that the first vector construct contains the following functional elements:
(a) Cytomegalovirus (CMV) enhancer/promoter,
(b) Multiple cloning site,
(c) Polyadenylation signal,
(d) DHFR expression cassette,
(e) Origin of replication,
(f) beta-lactamase expression cassette for Ampicillin-resistance in bacteria.

The invention specifically relates to a cell, a representative of which is deposited with the DSMZ (Deutsche Sammlung von Mikroorganismen und Zellkulturen GmbH) under the number DSM ACC2909. The invention also specifically relates to a cell, a representative of which is deposited with the DSMZ (Deutsche Sammlung von Mikroorganismen und Zellkulturen GmbH) under the number DSM ACC2910.

The invention specifically relates to a cell deposited with the DSMZ (Deutsche Sammlung von Mikroorganismen und Zellkulturen GmbH) under the number DSM ACC2909. The invention also specifically relates to a cell deposited with the DSMZ under the number DSM ACC2910.

In a preferred embodiment of the present invention said cell is characterized in that the cell additionally comprises a second vector construct comprising a gene of interest encoding a protein of interest. Preferably said second vector construct comprises a selection and/or amplification marker other than DHFR. Preferably said selection and/or amplification marker other than DHFR is selected from a group consisting of: Metallothionein, CAD (Carbamoyl-phosphate synthetase:Aspartate transcarbamylase: Dihydroorotase), Adenosine deaminase, AMP (adenylate) deaminase, UMP synthase, IMP 5'dehydrogenase, Xanthine-guanine phosphoribosyltransferase, Mutant HGPRTase or mutant thymidine kinase, Thymidylate synthetase, P-glycoprotein 170 (MDR1), Ribonucleotide reductase, Glutamine synthetase, Asparagine synthetase, Argininosuccinate synthetase, Omithine decarboxylase, HMG-CoA reductase, N-Acetylglucosaminyl transferase, Threonyl-tRNA synthetase and $Na^+K^+$-ATPase.

In a preferred embodiment said selection and/or amplification marker is gluthamine synthetase (GS).

The invention particularly relates to a cell line, a representative of which is deposited with the DSMZ (Deutsche Sammlung von Mikroorganismen und Zellkulturen GmbH) under the number DSM ACC2909. The invention particularly relates to a cell line deposited with the DSMZ under the number DSM ACC2909. Preferably said cell line is characterized by having a higher DHFR expression level than wild type (WT) CHO cells, which is measurable by quantitative RT PCR assay.

In a preferred embodiment the cell line, a representative of which is deposited with the DSMZ under the number DSM ACC2909 additionally comprises a second vector construct comprising a gene of interest encoding a protein of interest and a selection and/or amplification marker other than DHFR. Preferably said selection and/or amplification marker other than DHFR is selected from the group consisting of: Metallothionein, CAD (Carbamoyl-phosphate synthetase:Aspartate transcarbamylase: Dihydroorotase), Adenosine deaminase, AMP (adenylate) deaminase, UMP synthase, IMP 5'dehydrogenase, Xanthine-guanine phosphoribosyltransferase, Mutant HGPRTase or mutant thymidine kinase, Thymidylate synthetase, P-glycoprotein 170 (MDR1), Ribonucleotide reductase, Glutamine synthetase, Asparagine synthetase, Argininosuccinate synthetase, Omithine decarboxylase, HMG-CoA reductase, N-Acetylglucosaminyl transferase, Threonyl-tRNA synthetase and $Na^+K^+$-ATPase.

Preferably said selection and/or amplification marker on the second vector construct is gluthamine synthetase (GS).

The invention particularly relates to a cell line, a representative of which is deposited with the DSMZ (Deutsche Sammlung von Mikroorganismen und Zellkulturen GmbH) under the number DSM ACC2910. The invention particularly relates to a cell line deposited with the DSMZ under the number DSM ACC2910. In a specific embodiment said cell line is characterized by having a DHFR expression level between wild type CHO cells and CHO DG44 cells, which is measurable by RT PCR assay. In another specific embodiment said cell line is characterized by having a growth profile in a production process, which is comparable to that of a CHO DG44 producer cell line which has been generated using the DHFR selection system and subsequent gene amplification using methotrexate (MTX).

In a preferred embodiment of the present invention said cell is characterized in that the cell additionally comprises a second vector construct comprising a gene of interest encoding a protein of interest. Preferably said second vector construct comprises a selection and/or amplification marker other than DHFR. Preferably said selection and/or amplification marker other than DHFR is selected from a group consisting of: Metallothionein, CAD (Carbamoyl-phosphate synthetase:Aspartate transcarbamylase: Dihydroorotase), Adenosine deaminase, AMP (adenylate) deaminase, UMP synthase, IMP 5'dehydrogenase, Xanthine-guanine phosphoribosyltransferase, Mutant HGPRTase or mutant thymidine kinase, Thymidylate synthetase, P-glycoprotein 170 (MDR1), Ribonucleotide reductase, Glutamine synthetase, Asparagine synthetase, Argininosuccinate synthetase, Omithine decarboxylase, HMG-CoA reductase, N-Acetylglucosaminyl transferase, Threonyl-tRNA synthetase and $Na^+K^+$-ATPase.

In a preferred embodiment said selection and/or amplification marker is gluthamine synthetase (GS).

The invention further relates to the use of a cell line, a representative of which is deposited with the DSMZ (Deutsche Sammlung von Mikroorganismen und Zellkulturen GmbH) under the number DSM ACC2910 (CHOpper® Standard), as a model cell for production cell proteomics. The invention further relates to the use of a cell deposited with the DSMZ under the number DSM ACC2910 (CHOpper® Standard), as a model cell for production cell proteomics.

The invention further relates to a method for generating a host cell line such as the cell line, (a representative of which is) deposited at the DSMZ under the number DSM ACC2909 (CHOpper® Discovery), characterized by the following steps:

(a) Providing a cell with no or low endogenous DHFR levels,
(b) Introducing a DHFR expression cassette, which comprises a DHFR minigene (preferably comprising exon 1, intron 1 and exon 2 of the hamster DHFR gene), located on a first vector construct into said cell of step a),
(c) Selecting for a stably transfected cell population,
(d) Screening for the fastest growing cell population showing a high integral of viable cells over time (IVC) in batch and/or fed batch culture; whereby the IVC of said cell population is enhanced at least 2-fold compared to the parental cell of step (a),
(e) Generating a monoclonal cell line from the cell population of step (d),
(f) Screening the cells of step (e) for the level of DHFR expression and the growth properties in batch and/or fed-batch cultures,
(g) Selecting for a cell showing higher DHFR expression than a wildtype cell and an IVC at day 5 in fed-batch culture which is at least 2-fold higher compared to the parental cell line of step a).

In a preferred embodiment said monoclonal cell line is selected by FACS-based single-cell cloning.

The invention further relates to a cell generated by the method described above comprising the DHFR expression cassette, which comprises a DHFR minigene, whereby said cell has a higher DHFR expression than a wildtype cell and an IVC at day 5 in fed-batch culture which is at least 2-fold higher compared to the parental cell line. Preferably the DHFR minigene comprises or consists essentially of or consists of the first two exons of the DHFR gene, preferably of exon 1, intron 1 and exon 2. Most preferably, the DHFR minigene is derived from the hamster DHFR gene.

The invention further relates to a method for generating a host cell line such as the cell line, (a representative of which is) deposited at the DSMZ under the number DSM ACC2910 (CHOpper® Standard), characterized by the following steps
(a) Providing a cell with no or low endogenous DHFR levels,
(b) Introducing a DHFR expression cassette, which comprises a DHFR minigene (preferably comprising exon 1, intron 1 and exon 2 of the hamster DHFR gene), located on a first vector construct into said cell of step a),
(c) Selecting for a stably transfected cell population,
(d) Screening for the fastest growing cell population showing a high integral of viable cells over time (IVC) in batch and/or fed batch culture; whereby the IVC of said cell population is enhanced at least 2-fold compared to the parental cell of step (a)
(e) Generating a monoclonal cell line from the cell population of step (d),
(f) Screening the cells of step (e) for the level of DHFR expression and the growth properties in batch and/or fed-batch cultures,
(g) Selecting for a cell showing DHFR expression levels higher than the parental cell of step a) and an IVC at day 5 in fed-batch culture which is comparable/within a range of ±30% to the IVC of an amplified monoclonal DHFR-based production cell line.

In a preferred embodiment said monoclonal cell line is generated by FACS-based single-cell cloning.

The invention further relates to a cell generated by the above method comprising the DHFR expression cassette, which comprises a DHFR minigene, whereby said cell has a DHFR expression level higher than the parental cell and an IVC at day 5 in fed-batch culture which is comparable/within a range of ±30% to the IVC of an amplified monoclonal DHFR-based production cell line. Preferably the DHFR minigene comprises or consists essentially of or consists of the first two exons of the DHFR gene, preferably of exon 1, intron 1 and exon 2. Most preferably, the DHFR minigene is derived from the hamster DHFR gene.

In a specific embodiment of the above methods the steps are carried out sequentially. In another specific embodiment of the described methods the order of the steps is exchanged.

In a preferred embodiment of the methods the DHFR expression cassette consists essentially of or consists of the SEQ ID NO:5.

In a specific embodiment of the methods DHFR is the only mammalian expression unit which is introduced into said cell line during step b. In another specific embodiment of the methods a gene of interest is not introduced into said cell during step b.

In a preferred embodiment these methods additionally comprise the steps of:
(h) introducing a second expression cassette comprising a gene of interest encoding a protein of interest into said cell,
(i) selecting for a stably transfected cell population,
(j) generating a monoclonal cell line from said cell population, which expresses said gene of interest encoding said protein of interest.

In a preferred embodiment of any of said methods described above the DHFR minigene comprises only the first two exons of the DHFR gene. Preferably, the DHFR minigene comprises or consists essentially of or consists of the first two exons of the DHFR gene, preferably exon 1, intron 1, exon 2. Most preferably, the DHFR minigene is derived from the hamster DHFR gene.

The invention further relates to a method of producing a protein of interest encoded by a gene of interest in a cell having no or low endogenous DHFR expression levels characterized by the following steps:
(a) Providing a host cell as described above or
(b) Providing a host cell generated by a method as described above comprising a second vector construct comprising a gene of interest encoding a protein of interest,
(c) Cultivating the cells, under conditions which allow the proliferation of the cells and expression of at least the gene of interest,
(d) Harvesting the protein of interest and
(e) Purifying the protein of interest.

In a preferred embodiment said cell is a mammalian cell line.

In another preferred embodiment said cell of step (a) is a cell, (a representative of which is) deposited with the DSMZ under the number DSM ACC2909 (CHOpper® Discovery). In a further preferred embodiment said cell in step (a) is a cell, (a representative of which is) deposited with the DSMZ under the number DSM ACC2910 (CHOpper® Standard).

In a specifically preferred embodiment of said method the protein of interest is a secreted protein. Particularly preferred is a synthetic protein or a fusion protein which is secreted.

In a further preferred embodiment of said method of producing a protein the other selection marker on the second vector construct is glutamine synthetase (GS). In another preferred embodiment of said method of producing a protein the host cell comprises as selection and/or amplification marker for the gene of interest which is glutamine synthetase (GS).

The invention further relates to a method of identifying/characterizing the above described cell by a specific PCR band pattern/fingerprint when using genomic DNA as template, whereby: a 437 bp PCR product is generated using the oligonucleotide primers of SEQ ID NO: 1 and SEQ ID NO:2, and a 438 bp PCR product is generated using the oligonucleotide primers of SEQ ID NO: 6 and SEQ ID NO: 7, and a 928 bp PCR product is generated using the oligonucleotide primers of SEQ ID NO: 8 and SEQ ID NO: 10, and/or a 416 bp PCR product is generated using the oligonucleotide primers of SEQ ID NO: 9 and SEQ ID NO: 10.

The invention further relates to a method of identifying/characterizing the above described cell by a specific PCR band pattern/fingerprint when using genomic DNA as template, whereby: a 437 bp PCR product is generated using the oligonucleotide primers of SEQ ID NO: 1 and SEQ ID NO:2, and a 438 bp PCR product is generated using the oligonucleotide primers of SEQ ID NO: 6 and SEQ ID NO: 7, and a 928 bp PCR product is generated using the oligonucleotide primers of SEQ ID NO: 8 and SEQ ID NO: 10.

The invention further relates to a method of identifying/characterizing the above described cell by a specific PCR band pattern/fingerprint when using genomic DNA as template, whereby: a 437 bp PCR product is generated using the oligonucleotide primers of SEQ ID NO: 1 and SEQ ID NO:2, and a 438 bp PCR product is generated using the oligonucleotide primers of SEQ ID NO: 6 and SEQ ID NO: 7, and a 928 bp PCR product is generated using the oligonucleotide primers of SEQ ID NO: 9 and SEQ ID NO: 10.

The invention further relates to a use of the described cell of the present invention for the manufacturing of proteins.

The invention preferably relates to a use of the cell of the present invention for diagnostic or research applications, for the production of recombinant proteins using selection and/or amplification systems other than DHFR (e.g. the glutamine synthetase (GS) system, for the isolation and/or characterization of cellular components such as e.g. proteins, nucleic acids, organelles, membrane fractions, for the generation of conditioned medium or as feeder cells, preferably autologous feeder cells. Preferably the cell of the present invention is used as reference/"mock"/control cell in cell engineering approaches or proteomics studies.

The invention further relates to a kit comprising a cell of the present invention, an expression vector and a cell culture medium for cultivation of said cell. The invention specifically relates to a kit consisting of a cell of the present invention, an expression vector and a cell culture medium for cultivation of said cell. Preferably said kit consists of a cell deposited with the DSMZ under the number DSM ACC2909 (CHOpper® Discovery) or DSM ACC2910 (CHOpper® Standard), an expression vector and a cell culture medium for cultivation of said cell. Most preferably the cell in said kit is a cell deposited with the DSMZ under the number DSM ACC2909 (CHOpper® Discovery).

Preferably said expression vector is suitable for the expression of a gene of interest encoding a protein of interest, said expression vector containing a selection and/or amplification marker other than DHFR. Preferably said selection and/or amplification marker is selected from a group consisting of: Metallothionein, CAD (Carbamoyl-phosphate synthetase: Aspartate transcarbamylase: Dihydroorotase), Adenosine deaminase, AMP (adenylate) deaminase, UMP synthase, IMP 5'dehydrogenase, Xanthine-guanine phosphoribosyl-transferase, Mutant HGPRTase or mutant thymidine kinase, Thymidylate synthetase, P-glycoprotein 170 (MDR1), Ribonucleotide reductase, Glutamine synthetase, Asparagine synthetase, Argininosuccinate synthetase, Ornithine decarboxylase, HMG-CoA reductase, N-Acetylglucosaminyl transferase, Threonyl-tRNA synthetase and $Na^+K^+$-ATPase. Most preferably, said selection and/or amplification marker is Glutamine synthetase (GS).

The invention furthermore relates to a kit comprising a cell of the present invention and an expression vector. Preferably said cell is a cell deposited with the DSMZ under the number DSM ACC2909 (CHOpper® Discovery) or DSM ACC2910 (CHOpper® Standard), most preferably said cell is a cell deposited with the DSMZ under the number DSM ACC2909 (CHOpper® Discovery).

The invention generally described above will be more readily understood by reference to the following examples, which are hereby included merely for the purpose of illustration of certain embodiments of the present invention and are not intended to limit the invention in any way.

EXAMPLES

Materials and Methods
Cell Culture

All cell lines used at production and development scale are maintained in serial seedstock cultures in surface-aerated T-flasks (Nunc, Denmark) in incubators (Thermo, Germany) or shake flasks (Nunc, Denmark) at a temperature of 37° C. and in an atmosphere containing 5% $CO_2$. Seedstock cultures are subcultivated every 2-3 days with seeding densities of 1-3E5 cells/mL. The cell concentration is determined in all cultures by using a hemocytometer. Viability is assessed by the trypan blue exclusion method.

Fed-batch Cultivation

Cells are seeded at 3E05 cells/ml into 125 ml shake flasks in 30 ml of BI-proprietary production medium without antibiotics or MTX (Sigma-Aldrich, Germany). The cultures are agitated at 120 rpm in 37° C. and 5% $CO_2$ which is reduced to 2% following day 3. BI-proprietary feed solution is added daily and pH is adjusted to pH 7.0 using $NaCO_3$ as needed. Cell densities and viability are determined by trypan-blue exclusion using an automated CEDEX cell quantification system (Innovatis).

Generation of Antibody-producing Cells

Cells from the cell line deposited with the DSMZ under the number DSM ACC2909 (CHOpper® Discovery) and CHO wild type cells (ECACC no. 8505302) are stably transfected with an expression plasmid encoding heavy and light chains of an IgG1-type antibody and the glutamine synthetase gene as selection marker. 24h hours after transfection, the cells are subjected to selection by seeding into glutamine-free medium containing methionine sulfoximine (Sigma-Aldrich, Germany) at concentrations of 2 µM for CHOpper® Discovery and 15 µM MSX for CHO wild type cells. After about 3 weeks of selection, stable cell populations are obtained and further cultivated according to a standard stock culture regime with subcultivation every 2 to 3 days.

Determination of Recombinant Product Concentration by ELISA

To assess recombinant antibody production in transfected cells of the cell line deposited with the DSMZ under the number DSM ACC2909 (CHOpper® Discovery) and CHO wild type cells, samples from cell supernatant are collected from standard inoculum cultures at the end of each passage for three consecutive passages. The product concentration is then analysed by enzyme linked immunosorbent assay (ELISA). The concentration of secreted monoclonal antibody product is measured using antibodies against human-Fc fragment (Jackson Immuno Research Laboratories) and human kappa light chain HRP conjugated (Sigma).

Single Cell Sorting

A FACS Vantage (Becton Dickinson) flow cytometer equipped with pulse processing, sort enhancement module, and automatic cell deposition unit is used for analysis and cell sorting. On a dot plot of forward and side scatter (FSC/SSC) a gate is set around single living cells. Sorted cells are deposited into 96-well microtiter plates containing 200 µL growth medium at one cell per well with the automatic cell deposition unit.

Nucleic Acid Isolation and RT-PCR

Genomic DNA and total RNA from growing cells are isolated using TRIzol® reagent (Invitrogen, Germany) according to the manufacturer's instructions. The RNA is then treated with DNase I for 30 minutes at 37° C. First strand cDNA synthesis is carried out using the Cloned AMV First-Strand cDNA Synthesis Kit (Invitrogen, Germany) starting with 3 µg of total RNA and oligo(dT) oligonucleotides.

Quantitative differences in dhfr transcript levels are determined by real-time PCR using the Absolute™ QPCR SYBR® Green Fluorescein Mix (ABgene, Surrey, UK) and a thermal cycler controlled by the MyIQ Real Time Detection software (BioRad, Germany). All experiments are performed in triplicates.

DHFR-specific transcripts are detected and quantified relative to tubulin expression levels using oligonucleotide primers: DHFR sense: 5-ATG GTT CGA CCG CTG AAC TGC-3' (SEQ ID NO: 1), DHFR anti-sense: 5'-CCA CTG AGG AGG TGG TGG TCA TT-3' (SEQ ID NO: 2), Tubulin sense: 5'-CTC AAC GCC GAC CTG CGC AAG-3' (SEQ ID NO: 3), Tubulin anti-sense: 5'-ACT CGC TGG TGT ACC AGT GC-3' (SEQ ID NO: 4).

Differential Two-dimensional Gel Electrophoresis (2D-DIGE) Proteomics Analysis of CHO Culture Supernatants
Sample Preparation and Labelling Differential two-dimensional gel electrophoresis (2D-DIGE) is based on labelling two samples with different fluorescent dyes. When the proteins of both samples are separated by 2D electrophoresis on a single gel, the individual protein abundance of each spot can be assigned to the corresponding sample.

For 2D-DIGE analysis, CHOpper® Standard® cells are cultivated in shake flasks with a seeding cell density of 3×10⁵ cells/mL. At different time points during the fermentation process, supernatant samples are collected and cleared from cells by centrifugation for 10 min 3000 g. Clear supernatant is concentrated 60 to 100-fold by repeated centrifugation in Vivaspin columns with a molecular cut-off size of 10 kD and 5 kD (polyethersulfone membrane (PES), Sartorius, Goettingen, Germany) at 4° C. Following concentration, samples are washed and re-dissolved in DIGE buffer. Protein concentration is determined using the thiourea-compatible Bradford protein assay (BioRad).

As a next step, samples are labelled with 400 pmol of either Cy3 or Cy5 fluorescent dyes (GE Healthcare) for comparison on the same gel. Labelling reactions are performed on ice in the dark for 30 min and then quenched with a 50-fold molar excess of free lysine to dye for 10 min on ice. An internal standard containing a pool of all samples (both control and test) is labelled with Cy2 fluorescent dye, and this was used as a standard on all gels to aid image matching and cross-gel statistical analysis. The Cy3 and Cy5 labelling reactions (50 μg of each) from each lysate are mixed and run on the same gels together with the Cy2-labelled standard.

2D-DIGE

For analytical gels, the sample loading onto a 24 cm Immobiline DryStrip® pH 3-10 NL (GE Healthcare, Munich, Germany) is performed by in-gel rehydration. The sample is added to the focusing tray of the PROTEAN IEF Cell (Bio-Rad, Hercules, USA) and the precast IPG strip is placed on top of the sample. The strips are focused in the PROTEAN IEF Cell (BioRad, Hercules, USA) at a constant temperature of 20° C. The strips are further rehydrated for about 12 h. Subsequently, an isoelectric focusing protocol comprising five steps of increasing voltages is applied: 1 h at 50V and 1 h at 100V, for a good sample entry, 1 h at 500V, 1 h at 1000V and 8 h at 8000 V for the focusing. At the end of the run about 55000 volt hours has been reached. After IEF, the strips are equilibrated for 15 min in 50 mM Tris-HCl pH 8.8, 6 M urea, 30% v/v glycerol, 1% w/v SDS supplemented with 65 mM DTT, followed by a second 15 min equilibration in the same buffer containing 240 mM iodoacetamide instead of DTT. The equilibrated strips are then transferred onto large format 9-18% polyacrylamide gradient gels (Tris-HCl Optigel-LF, 9-18% linear from Nextgenescience) and run using the Ettan DALT system (GE Healthcare, Munich, Germany) at 10 mA/gel for about 1 h and subsequently 15 mA/gel for 13-14 hours until the dye-front reaches the bottom of the gel. Gels are scanned using the Typhoon 9400 laser scanner (GE Healthcare, Munich, Germany) at an excitation/emission setting of 488/520 nm for Cy2, 532/580 nm for Cy3 and 633/670 nm for Cy5.

Image Acquisition and Data Analysis

The 2-D-DIGE analysis is performed using the DeCyder 2D™ Software 6.5 (GE Healthcare, Munich, Germany). Statistical analysis and quantification of protein abundance is carried out using the biological variation analysis module (BVA) of the DeCyder software. One gel is selected as master gel and all other gels in the study are matched to this master gel by the software. Selected spots are picked with the Ettan DALT Spot Picker (GE Healthcare, Munich, Germany), transferred into a 96-well plate with porous bottoms (Proxeon Biosystems, San Mateo, USA) and subjected to in gel digestion using trypsin. Digestion fragments are then analysed by tandem mass spectrometry using an UltiMate nanoHPLC system (Dionex, Sunnyvale, USA) connected to a QSTAR XL quadrupole time-of-flight hybrid mass spectrometer (Applied Biosystems, Foster City, USA). Subsequently, protein identity is determined by blasting the fragment sequences against the SwissProt database.

EXAMPLES

Generation & Characterization of CHOpper® Cells

Example 1

Generation of CHOpper® Cell Pools

DHFR-deficient CHO-DG44 (Urlaub & Chasin, Cell 33, 405-412; 1983) are stably transfected with a plasmid carrying a DHFR expression cassette (SEQ ID NO: 5, in 5'-3' orientation; Exons of the DHFR minigene are highlighted in grey and bold print. Start and stop codons are underlined):

```
TCAGGGAACTGAGGTTAAAAGATGTATCCTGGACCTGCCAGACCTGGCCA
TTCACGTAAACAGAAGATTCCGCCTCAAGTTCCGGTTAACAACAGGAGGC
AACGAGATCTCAAATCTATTACTTCTAATCGGGTAATTAAAACCTTTCAA
CTAAAACACGGACCCACGGATGTCACCCACTTTTCCTTCCCCGGCTCCGC
CCCTTCTCAGTACTCCCCACCATTAGGCTCGCTACTCTACCTCCACTTCC
GGGCGCGACACCCACGTGCCCTCTCCCACCCGACGCTAACCCCGCCCCTG
CCCGTCTGACCCCGCCCACCACCTGGCCCCGCCCCGTTGAGGACAGAAGA
AACCCCGGGCAGCCGCAGCCAAGGCGGAGCGGTAGACGCTGGGGGCGCTG
AGGAGTCGTCCTCTACCTTCTCTGCTGGCTCGGTGGGGGACGCGGTGGAT
CTCAGGCTTCCGGAAGACTGGAAGAACCGGCTCAGAACCGCTTGTCTCCG
CGGGGCTTGGGCGGCGGAAGAATGGCCGCTAGACGCGGACTTGGTGCGAG
GCATCGCAGGATGCAGAAGAGCAAGCCCGCCGGGAGCGCGCGGCTGTACT
ACCCCGCGCCTGCGAGCGCGCACGCCGCGACTGGGCGGGGCCGGCCTGGT
GGAGGCGGAGTCTGACCTCGTGGAGGCGGGGCCTCTGATGTTCAAATAGG
ATGCTAGGCTTGTTGAGGGCGTGGCCTCCGATTCACAAGTGGGAAGCAGC
CCGGGCGACTGCAATTTCGCGCCAAACTTGGGGGAAGCACAGCGTACAGG
CTGCCTAGGTGATCGCTGCTGCTGTCATGGTTCGACCGCTGAACTGCATC
GTCGCCGTGTCCCAGAATATGGGCATCGGCAAGAACGGAGACCTTCCCTG
GCCAATGCTCAGGTACTGGCTGGATTGGGTTAGGGAAACCGAGGCGGTTC
GCTGAATCGGGTCGAGCACTTGGCGGAGACGCGCGGGCCAACTACTTAGG
GACAGTCATGAGGGGTAGGCCCGCCGGCTGCTGCCCTTGCCCATGCCCGC
GGTGATCCCCATGCTGTGCCAGCCTTTGCCCAGAGGCGCTCTAGCTGGGA
GCAAAGTCCGGTCACTGGGCAGCACCACCCCCCGGACTTGCATGGGTAGC
CGCTGAGATGGAGCCTGAGCACACGTGACAGGGTCCCTGTTAACGCAGTG
TTTCTCTAACTTTCAGGAACGAGTTCAAGTACTTCCAAAGAATGACCACC
ACCTCCTCAGTGGAAGGTAAACAGAACCTGGTGATTATGGGCCGGAAAAC
CTGGTTCTCCATTCCTGAGAAGAATCGACCTTTAAAGGACAGAATTAATA
TAGTTCTCAGTAGAGAGCTCAAGGAACCACCACAAGGAGCTCATTTCCTT
GCCAAAAGTCTGGACGATGCCTTAAAACTTATTGAACAACCAGAGTTAGC
AGATAAAGTGGACATGGTTTGGATAGTTGGAGGCAGTTCCGTTTACAAGG
AAGCCATGAATCAGCCAGGCCATCTCAGACTCTTTGTGACAAGGATCATG
CAGGAATTTGAAATGACACGTTCTTCCCAGAAATTGATTTGGAGAAATAT
AAACTTCTCCCAGAGGTACCCAGGGGTCCTTTCTGAAGTCCAGGAGGAAA
AAGGCATCAAGTATAAATTTGAAGTCTATGAGAAGAAAGGCTAACAGAAA
GATACTTGCTGATTGACTTCAAGTTCTACTGCTTTCCTCCTAAAATTATG
CATTTTTACAAGACCATGGGACTTGTGTTGGCTTTAGATCCTGTGCATCC
TGGGCAACTGTTGTACTCTAAGCCACTCCCCAAAGTCATGCCCCAGCCCC
TGTATAATTCTAAACAATTAGAATTATTTTCATTTTCATTAGTCTAACCA
GGTTATATTAAATATACTTTAAGAAACACCATTTGCCATAAAGTTCTCAA
TGCCCCTCCCATGCAGCCTCAAGTGGCTCCCCAGCAGATGCATAGGGTAG
TGTGTGTACAAGAGACCCAAAGACATAGAGCCCCTGAGAGCATGAGCTGA
TATGGGGGCTCATAGAGATAGGAGCTAGATGAATAAGTACAAAGGGCAGA
AATGGGTTTTAAACAGCAGAGCTAGAACTCAGACTTTAAAGAAAATTAGA
TCAAAGTAGAGACTGAATTATTCTGCACATCAGACTCTGAGCAGAGTTCT
GTTCACTCAGACAGAAATGGGTAAATTGAGAGCTGGCTCCATTGTGCTC
CTTAGAGATGGGAGCAGGTGGAGGATTATATAAGGTCTGGAACATTTAAC
TTCTCCGTTTCTCATCTTCAGTGAGATTCCAAGGGATACT
```

Stably transfected cell pools are generated by selection in the absence of hypoxanthin and thymidine (HT) supplementation. Growth characteristics of the arising stable cell pools are analysed in seedstock cultures and during fed-batch cultivation in shake flasks which represent an established screening model for fermentation/production processes. For comparison, wild type CHO cells (ECACC no. 8505302), the parental CHO-DG44 cell line as well as CHO-DUX (B11) cells are included in these experiments.

FIG. 1 shows the growth profiles of all cell lines in a six day fed-batch process. DHFR-deficient CHO-DG44 as well as CHO DUX (B11) cells show markedly reduced cell growth and lower cell densities compared to wild type CHO cells and CHO-DG44 cells transfected with DHFR (which are herein referred to as "CHOpper®" cells). Surprisingly, heterologous introduction of DHFR does not only restore cell growth in DG44 cells, but CHOpper cells grow even faster than wild-type CHO cells.

These data are in agreement with markedly shortened doubling times in inoculum cultures (FIG. 3).

Example 2

Generation and Screening of Monoclonal CHOpper® Cell Lines

The fastest growing CHOpper cell pool is subjected to FACS-based single cell cloning to generate monoclonal CHOpper cell lines. The growth properties of the clones is then analysed in fed-batch fermentation runs. The parental CHO-DG44 cell line as well as three producer cell clones from independent cell line generation projects expressing different antibody products are included for comparison.

As shown in FIG. 2, all monoclonal CHOpper® cell lines grow markedly faster and reach far higher integrals of viable cells over time (IVCs) in fed batch cultures compared to CHO-DG44 cells. The level of growth improvement is heterogeneous, the difference compared to the parental cell line ranging from 2.5 to 6-fold within six days. Some of the CHOpper® clones show similar growth characteristics as the average of the three producer cell clones, but some CHOpper® clones even grow significantly faster.

From all CHOpper® clones generated we select two cell lines: the fastest growing cell line is deposited with the DSMZ under the number DSM ACC2909. We call this cell line CHOpper® Discovery" (FIGS. 2 and 3). Another cell line is selected for reflecting the growth behaviour of producer cell lines generated by a standard industrial cell line generation procedure based on the DHFR system and subsequent MTX-induced gene amplification. This cell line is deposited with the DSMZ under the number DSM ACC2910. This cell line is called "CHOpper® Standard" (FIG. 2).

We show that the improved growth characteristics directly correlate with the level of DHFR expression in the cells ("gene-dose effect"). In the next step, we therefore quantitatively analyse the levels of DHFR specific transcript in wild type CHO cells, parental CHO-DG44 cells and the selected CHOpper® clones by real-time PCR.

As shown in FIG. 4, wild type CHO cells express endogenous DHFR, whereas CHO DG44 cells completely lack DHFR transcripts. CHOpper® Discovery cells show DHFR expression levels which are even higher than those of wild-type cells, which is well in line with their growth properties during fermentation. Cells deposited with the DSMZ under the number DSM ACC2910 (CHOpper® Standard) also express DHFR, but in lower levels compared to wild type CHO cells.

Example 3

Characterization and Unique Identification of CHOpper® Cell Lines

CHOpper® cell lines can be described in general as cells with heterologous DHFR expression, whereby DHFR is not functionally linked/does not serve as selection marker for a gene of interest.

The CHOpper® cell lines described in the present invention contain a DHFR expression cassette as depicted in FIG. 5A (SEQ ID NO:5) comprising: Upstream regulatory sequences (825 bp) derived from the hamster DHFR gene including the DHFR promoter, DHFR minigene, comprising exon 1, intron 1 and exon 2 of the hamster DHFR gene, and TAA stop codon and 647 bp of the 3' untranslated region including polyadenylation signal.

The vector construct used for generation of the CHOpper® cell lines described in the present invention is shown in FIG. 5B and contains the following functional elements:
Cytomegalovirus (CMV) enhancer/promoter
Multiple cloning site
Polyadenylation signal
DHFR expression cassette
Origin of replication
beta-lactamase expression cassette for Ampicillin-resistance in bacteria CHOpper® cell lines containing the pBI-26 construct, such as the cell line deposited with the DSMZ under the number DSM ACC2909 (CHOpper® Discovery) and the cell line deposited with the DSMZ under the number DSM ACC2910 (CHOpper® Standard), can be identified by PCR on genomic DNA. A specific set of oligonucleotide primers (SEQ ID NOs:1, 2 and 6 to 10) produces a distinct signal pattern in this PCR reaction which allows to differentiate CHOpper® cells from wild type CHO, DHFR-deficient CHO cells as well as DG44-based producer cell lines. Binding positions and orientation of the primers is depicted in FIG. 5 (arrow heads). Sizes of expected amplificates in the different cell lines are summarized in TABLE 3.

TABLE 3

Primer sets and sizes of expected PCR products for identification of CHOpper ® cell lines

| Primer Set: | CMV for (SEQ ID NO: 6), Terminator rev (SEQ ID NO: 7) | DHFR for-A (SEQ ID NO: 8), SV40 rev (SEQ ID NO: 10) | DHFR for-B (SEQ ID NO: 9), SV40 rev (SEQ ID NO: 10) | DHFR sense (SEQ ID NO: 1), DHFR anti-sense (SEQ ID NO: 2) |
|---|---|---|---|---|
| CHOpper ® cell | 438 bp | 928 bp | 416 bp | 437 bp |
| CHO wild type | — | — | — | 437 bp |
| CHO DG44 | — | — | — | — |
| DG44 producer cell | 438 bp + size of product gene | 928 bp | 416 bp | 437 bp |

TABLE 3-continued

Primer sets and sizes of expected PCR products for identification of CHOpper® cell lines

| | | |
|---|---|---|
| DHFR sense: | 5-ATG GTT CGA CCG CTG AAC TGC-3' | (SEQ ID NO: 1) |
| DHFR anti-sense: | 5'-CCA CTG AGG AGG TGG TGG TCA TT-3' | (SEQ ID NO: 2) |
| CMV for: | 5'-GGC GTG GAT AGC GGT TTG ACT C-3' | (SEQ ID NO: 6) |
| Terminator rev: | 5'-ACC ACC CTGC CAT CCC ACA ACA G-3' | (SEQ ID NO: 7) |
| DHFR for-A: | 5'-CTG CTT TCC TCC TAA AAT TAT GCA-3' | (SEQ ID NO: 8) |
| DHFR for-B: | 5'-CCA TTG TGC TCC TTA GAG AT-3' | (SEQ ID NO: 9) |
| SV40 rev: | 5'-CCT CCT CAC TAC TTC TGG AAT A-3' | (SEQ ID NO: 10) |

The level of DHFR expression as measured by real-time PCR (FIG. 4) shows:

for the cell line deposited with the DSMZ under the number DSM ACC2909 (CHOpper® Discovery): high DHFR expression, levels being higher than in wild type CHO cells for the cell line deposited with the DSMZ under the number DSM ACC2910 (CHOpper® Standard): DHFR expression levels between those detected in CHO DG44 and CHO wild type cells.

Both CHOpper® cell lines described in the present invention have doubling times below 24 hrs in standard inoculum cultures and without using peptones or other growth-promoting medium additives. The doubling time of the cell line deposited with the DSMZ under the number DSM ACC2910 (CHOpper® Standard) is below 22 hrs, the doubling time of the cell line deposited with the DSMZ under the number DSM ACC2909 (CHOpper® Discovery) is even below 18 hours (~17 hrs)

The two cell lines CHOpper® Discovery and CHOpper® Standard have been send to the DSMZ for patent deposit in Mai 2008 and have been assigned the following designations: DSM ACC2909 for the CHOpper® Discovery cell line and DSM ACC2910 for the CHOpper® Standard cell line. The cell line deposited with the DSMZ under the number DSM ACC2909 (CHOpper® Discovery) and the cell line deposited with the DSMZ under the number DSM ACC2910 (CHOpper® Standard) contain the DHFR expression cassette stably integrated into their genomes.

EXAMPLES

Applications

Example 4

CHOpper® Cells as Host Cells Recombinant Protein Production Using the GS System

Cells deposited with the DSMZ under the number DSM ACC2909 (CHOpper® Discovery) are ideal host cells for recombinant protein production. Particularly, due to their optimized growth and no further requirement of exogenous DHFR, they are very well suited for use of the GS system which in the literature has been described to provide higher basal levels of product expression compared to the DHFR system without need for further amplification.

In order to test this hypothesis, cells deposited with the DSMZ under the number DSM ACC2909 (CHOpper® Discovery) and CHO wild type cells (obtained from ECACC no. 8505302) are transfected with expression constructs encoding both chains of a human monoclonal IgG1-type antibody and bearing a glutamine synthetase gene for selection (see e.g. FIG. 7). Following transfection, stably IgG-producing cell populations are generated by selection in glutamine-free medium in the presence of methionine sulfoximine (MSX). The resulting stable cell pools are than subjected to standard inoculum-type cultivation with subcultivation every 2-3 days. At the end of each passages, samples from the culture supernatant of IgG-producing cells deposited with the DSMZ under the number DSM ACC2909 (CHOpper® Discovery) and CHO wild type cells are taken and antibody titers are determined during three consecutive passages.

As seen in FIG. 6, antibody concentrations in all CHOpper® Discovery cell pools are significantly higher compared to the titers measured in stably transfected wild type cells, the average difference ranging from 2-4-fold.

Thus, cells deposited with the DSMZ under the number DSM ACC2909 (CHOpper® Discovery) are not only suited for use of the GS system for recombinant protein production but they also yield higher product titers than wild type CHO cells in a side-by-side comparison.

Example 5

CHOpper® Standard As Reference Cell for Proteomics Approaches

Proteomics analysis from cell-free cell culture samples of production cells is hindered by the dominant presence of the recombinant protein product which is secreted by the producer cell. As shown on the silver gel in FIG. 8A, fresh culture medium does not contain proteins in detectable amounts. In comparison, a CHO-DG44 host cell line secretes a wide spectrum of different proteins which appear as faint bands in the silver gel. However, in CHO-DG44-derived antibody producer cell lines, the most prominent band at a molecular size of about 150 kDa represents the recombinant antibody product.

The cells deposited with the DSMZ under the number DSM ACC2910 (CHOpper® Standard) of the present invention are used as a reference cell line.

FIG. 8B represent a typical mastergel generated using a 2D-DIGE (two-dimensional differential gel electrophoresis) approach: Cell culture supernatant from a fermentation process using the CHOpper® Standard cell line is concentrated 100-fold and separated on a preparative 2D-gelelectrophoresis: In the vertical dimension, the proteins are separated by size (in the range of 15-150 kDa) and horizontally according to their charge in a pH-gradient (pH 3-10). As seen in FIG. 8B, a broad spectrum of different proteins present in the cell supernatant can be nicely separated by this technique, allowing for the detection of a multitude of different spots with sufficient resolution to be recognized by an automated software, annotated and picked for further analysis.

Example 6

Production of an IGG1 Antibody (MAB1)

Cells deposited with the DSMZ under the number DSM ACC2909 (CHOpper® Discovery) and CHO DG44 cells are transfected with expression constructs encoding a monoclonal IgG1-subtype antibody (MAB1). Following transfection, stably IgG-producing cell populations are generated by in the case of CHOpper® Discovery selection in glutamine-free medium in the presence of methionine sulfoximine (MSX) or medium without HT and in the presence of G418 and MTX in the case of DG44 cells. The resulting stable cell pools are then subjected to standard inoculum-type cultivation with subcultivation every 2-3 days. At the end of each passages, samples from the culture supernatant of IgG-producing cells are taken and specific antibody productivities are determined by ELISA during three consecutive passages. The table in FIG. 9 summarizes the timelines from transfection until completion of the pool phase for both cell line development approaches as well as the specific productivities of the top three pools.

As seen in FIG. 9, development of MAB1 producer cells originating from CHOpper® Discovery cells is faster and allows to reduce timelines by about one month compared to the classic DG44 timeline without negative impact on the specific productivities which are comparable between the top three pools from both approaches.

Thus, cells deposited with the DSMZ under the number DSM ACC2909 (CHOpper® Discovery) are not only suited for use of the GS system for recombinant antibody production but they also allow for a fast track cell line development program while yielding producer cell lines with specific productivities comparable to the classic DG44 program in a side-by-side comparison.

Example 7

Production of Another IGG1 Antibody MAB2

Cells deposited with the DSMZ under the number DSM ACC2909 (CHOpper® Discovery) are transfected with expression constructs encoding a human monoclonal IgG1-type antibody (MAB2). Following transfection, stable IgG1-producing cell populations are generated by selection in glutamine-free medium in the presence of methionine sulfoximine (MSX). The resulting stable cell pools are subjected to fed-batch culture for production of MAB2 material. For this purpose, the cells are seeded at 0.3 mio. cells/ml and feeded every 24 hrs from day three on. As seen in the growth profile in FIG. 10A, CHOpper® Discovery-based producer cell lines grow rapidly and reach peak cell densities of nearly 20 mio. cells/ml after seven days. Correspondingly, the integral of viable cells (IVC; FIG. 10B) is high in those processes, which is particularly favorable in production schemes aiming for short processes (of <15 days) and multiple harvests a week.

| SEQUENCE TABLE: | |
|---|---|
| SEQ ID NO: 1 | Primer DHFR sense |
| SEQ ID NO: 2 | Primer DHFR anti-sense |
| SEQ ID NO: 3 | Primer Tubulin sense |
| SEQ ID NO: 4 | Primer Tubulin anti-sense |
| SEQ ID NO: 5 | DHFR expression cassette |
| SEQ ID NO: 6 | Primer CMV for |
| SEQ ID NO: 7 | Primer Terminator rev |
| SEQ ID NO: 8 | Primer DHFR for-A |
| SEQ ID NO: 9 | Primer DHFR for-B |
| SEQ ID NO: 10 | Primer SV40 rev |

REFERENCE LIST

Alt, F. W., Kellems, R. E., Bertino, J. R., and Schimke, R. T. (1978). Selective multiplication of dihydrofolate reductase genes in methotrexate-resistant variants of cultured murine cells. J. Biol. Chem. 253, 1357-1370.

Asselbergs, F. A. and Widmer, R. (1995). Use of the *Escherichia coli* chromosomal DHFR gene as selection marker in mammalian cells. J. Biotechnol. 43, 133-138.

Bailey, J. E., Da Silva, N. A., Peretti, S. W., Seo, J. H., and Srienc, F. (1986). Studies of host-plasmid interactions in recombinant microorganisms. Ann. N. Y. Acad. Sci. 469, 194-211.

Fouser, L. A., Swanberg, S. L., Lin, B. Y., Benedict, M., Kelleher, K., Cumming, D. A., and Riedel, G. E. (1992). High level expression on a chimeric anti-ganglioside GD2 antibody: genomic kappa sequences improve expression in COS and CHO cells. Biotechnology (N. Y. ) 10, 1121-1127.

Gu, M. B., Kem, J. A., Todd, P., and Kompala, D. S. (1992). Effect of amplification of dhfr and lac Z genes on growth and beta-galactosidase expression in suspension cultures of recombinant CHO cells. Cytotechnology 9, 237-245.

Kaufman, R. J. (1990). Selection and coamplification of heterologous genes in mammalian cells. Methods Enzymol. 185, 537-566.

Kaufman, R. J. and Sharp, P. A. (1982). Amplification and expression of sequences cotransfected with a modular dihydrofolate reductase complementary dna gene. J. Mol. Biol. 159, 601-621.

Kaufman, R. J., Murtha, P., Ingolia, D. E., Yeung, C. Y., and Kellems, R. E. (1986). Selection and amplification of heterologous genes encoding adenosine deaminase in mammalian cells. Proc. Natl. Acad. Sci. U. S. A 83, 3136-3140.

Page, M. J. and Sydenham, M. A. (1991). High level expression of the humanized monoclonal antibody Campath-1H in Chinese hamster ovary cells. Biotechnology (N.Y.) 9, 64-68.

Pallavicini, M. G., Deteresa, P. S., Rosette, C., Gray, J. W., and Wurm, F. M. (1990). Effects of methotrexate on transfected DNA stability in mammalian cells. Mol. Cell Biol. 10, 401-404.

Pendse, G. J., Karkare, S., and Bailey, J. E. (1992). Effect of cloned gene dosage on cell growth and hepatitis B surface antigen synthesis and secretion in recombinant CHO cells. Biotechnology and Bioengineering 40, 119-129.

Puck, T. T. (1957). The genetics of somatic mammalian cells. Adv. Biol. Med. Phys. 5, 75-101.

Schimke, R. T., Kaufman, R. J., Alt, F. W., and Kellems, R. F. (1978). Gene amplification and drug resistance in cultured murine cells. Science 202, 1051-1055.

Simonsen, C. C. and Levinson, A. D. (1983). Isolation and expression of an altered mouse dihydrofolate reductase cDNA. Proc. Natl. Acad. Sci. U. S. A 80, 2495-2499.

Snapka, R. M., Ge, S., Trask, J., and Robertson, F. (1997). Unbalanced growth in mouse cells with amplified dhfr genes. Cell Prolif. 30, 385-399.

Urlaub, G. and Chasin, L. A. (1980). Isolation of Chinese hamster cell mutants deficient in dihydrofolate reductase activity. Proc. Natl. Acad. Sci. U. S. A 77, 4216-4220.

Urlaub, G., Kas, E., Carothers, A. M., and Chasin, L. A. (1983). Deletion of the diploid dihydrofolate reductase locus from cultured mammalian cells. Cell 33, 405-412.

Wurm, F. M. and Jordan, M. (2003). Gene Transfer and Gene Amplification in Mammalian Cells. In: Gene Transfer and Expression in Mammalian Cells, ed. S.C.Makrides Elsevier Science B.V., 309-335.

The invention claimed is:

1. An isolated cell with no or low endogenous DHFR levels comprising at least two heterologous vector constructs, whereby
   (a) A first vector construct comprises a DHFR expression cassette, which comprises:
      i. an upstream regulatory sequence including a DHFR promoter,
      ii. a DHFR minigene,
      iii. a polyadenylation signal,
      whereby said first vector construct does not contain a gene of interest nor another expression cassette encoding a eukaryotic protein, and
   (b) A second vector construct comprises a gene of interest and a selection and/or amplification marker other than DHFR,
   whereby the DHFR minigene comprises only the first two exons of the DHFR gene.

2. The cell according to claim 1, whereby the vector constructs are stably integrated into the cells genome.

3. The cell according to claim 2, whereby said cell is characterized by a specific PCR band pattern/fingerprint when using genomic DNA as template,
   whereby:
   (a) a 437 by PCR product is generated using the oligonucleotide primers of SEQ ID NO: 1 and SEQ ID NO:2, and
   (b) a 438 by PCR product is generated using the oligonucleotide primers of SEQ ID NO: 6 and SEQ ID NO: 7, and
   (c) a 928 by PCR product is generated using the oligonucleotide primers of SEQ ID NO: 8 and SEQ ID NO: 10, and/or
   (d) a 416 by PCR product is generated using the oligonucleotide primers of SEQ ID NO: 9 and SEQ ID NO: 10.

4. The cell according to claim 1, whereby said cell is a CHO cell with no endogenous DHFR level.

5. The cell according to claim 1, whereby the DHFR expression cassette consists of the SEQ ID NO: 5.

6. The cell according to claim 1, whereby said selection and/or amplification marker on the second vector construct is gluthamine synthetase (GS).

7. A cell deposited with the DSMZ under the number DSM ACC2909.

8. The cell according to claim 7, whereby said cell additionally contains a second vector construct comprising a gene of interest encoding a protein of interest and a selection and/or amplification marker other than DHFR.

9. A cell deposited with the DSMZ under the number DSM ACC2910.

10. The cell according to claim 9, whereby the cell additionally contains a second vector construct comprising a gene of interest encoding a protein of interest and a selection and/or amplification marker other than DHFR.

11. A kit comprising the cell according to claim 1, an expression vector and a cell culture medium.

12. A kit comprising the cell according to claim 7, an expression vector and a cell culture medium.

13. A kit comprising the cell according to claim 9, an expression vector and a cell culture medium.

* * * * *